United States Patent [19]

Yoshioka et al.

[11] Patent Number: 5,615,279

[45] Date of Patent: Mar. 25, 1997

[54] METHOD OF AND APPARATUS FOR CORRECTING SCATTERED X-RAYS FOR X-RAY COMPUTERIZED TOMOGRAPH

[75] Inventors: Tomonori Yoshioka, Kashiwa; Shinichi Migita, Ryugasaki; Tetsuo Nakazawa, Nagareyama, all of Japan

[73] Assignee: Hitachi Medical Corporation, Tokyo, Japan

[21] Appl. No.: 332,090

[22] Filed: Nov. 1, 1994

[30] Foreign Application Priority Data

Nov. 2, 1993 [JP] Japan .................................. 5-274171

[51] Int. Cl.⁶ ............................................ G06K 9/36
[52] U.S. Cl. ............................... 382/131; 382/275; 378/7
[58] Field of Search ........................... 382/128, 131, 382/132, 275; 364/413.14, 413.16; 378/7, 86, 87

[56] References Cited

U.S. PATENT DOCUMENTS

| | | | |
|---|---|---|---|
| 4,081,681 | 3/1978 | Froggatt | 250/360 |
| 4,656,650 | 4/1987 | Kikuchi et al. | 378/7 |
| 4,785,401 | 11/1988 | Harding et al. | 364/413.16 |
| 4,918,713 | 4/1990 | Honda | 378/99 |
| 5,440,647 | 8/1995 | Floyd, Jr. et al. | 382/132 |

FOREIGN PATENT DOCUMENTS

| | | | |
|---|---|---|---|
| 62-60539 | 3/1987 | Japan | A61B 6/03 |
| 62-270137 | 11/1987 | Japan | A61B 6/03 |
| 62-261342 | 11/1987 | Japan | A61B 6/03 |
| 63-38438 | 2/1988 | Japan | A61B 6/03 |
| 63-40534 | 2/1988 | Japan | A61B 6/03 |
| 63-305846 | 12/1988 | Japan | A61B 6/03 |
| 64-62126 | 3/1989 | Japan | A61B 6/03 |
| 4-170942 | 6/1992 | Japan | A61B 6/03 |
| 4-336044 | 11/1992 | Japan | A61B 6/03 |

*Primary Examiner*—Andrew Johns
*Attorney, Agent, or Firm*—Antonelli, Terry, Stout & Kraus, LLP

[57] ABSTRACT

In a scattered X-ray correction method for an X-ray computerized tomograph, the quantity of X-rays passed through a phantom is measured to be converted into logarithms. Obtained from the logarithmic data is a scattered X-ray correction curve representing a relationship between the measured data in the logarithmic expression and an amount of scattered X-ray correction. For a subject, the quantity of X-rays penetrated therethrough is measured to be transformed into logarithms. From the measured data undergone the logarithmic conversion and the scattered X-ray correction curve, there is attained a scattered X-ray correction amount in a linear region which is the state before the logarithmic conversion. The measured data of the subject in the logarithmic expression is subjected to an inverse logarithmic conversion. From the obtained values, the scattered X-ray correction amount is subtracted such that the resultant values are again converted into logarithms, thereby producing a computerized tomogram from the logarithmic values.

26 Claims, 18 Drawing Sheets

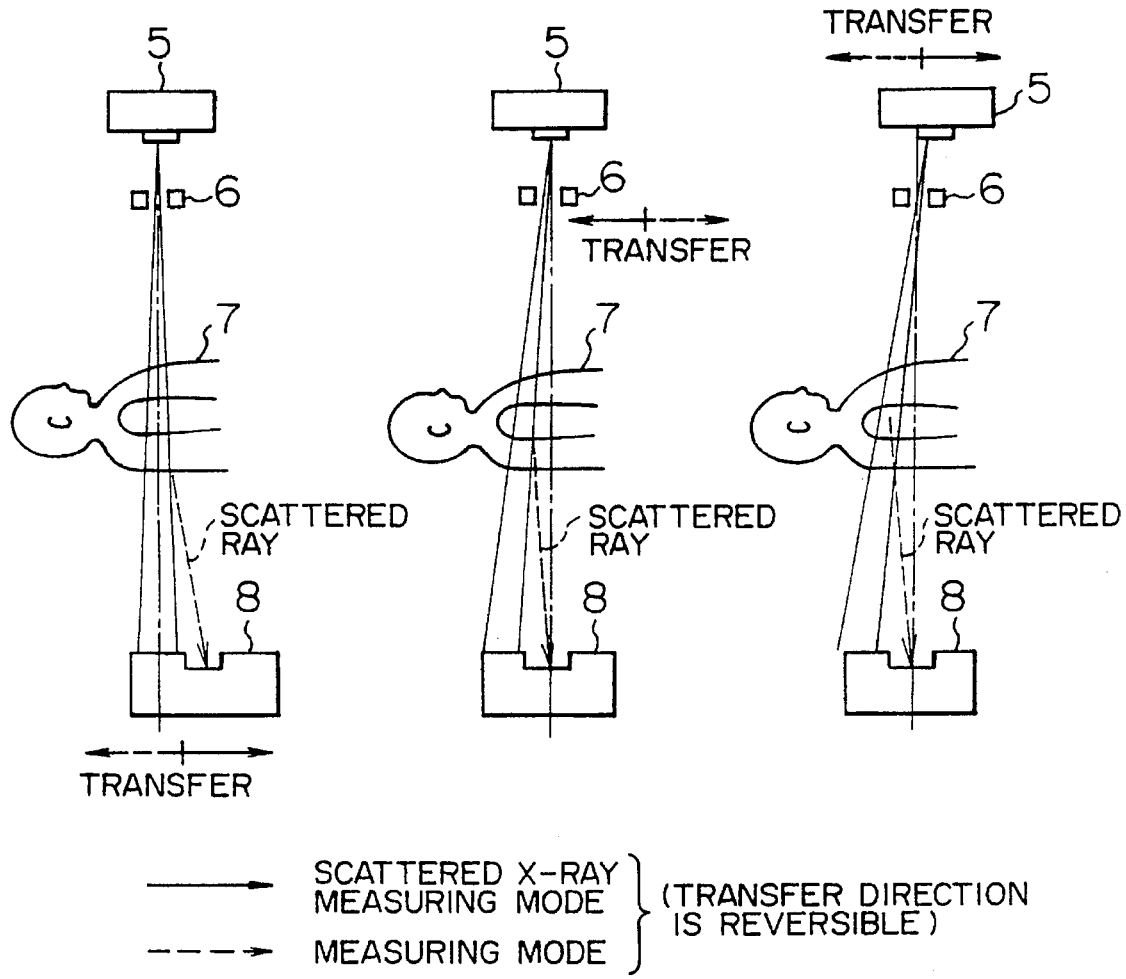

METHOD OF AND APPARATUS FOR CORRECTING SCATTERED X-RAYS FOR X-RAY COMPUTERIZED TOMOGRAPH

BACKGROUND OF THE INVENTION

The present invention relates to a scattered X-ray correcting method, an X-ray computerized tomograph (CT), and a multi-channel X-ray sensor, and in particular, to an X-ray CT having a mechanism for correcting influence of scattered X-rays and a multi-channel X-ray sensor having a function to sense scattered rays.

In an X-ray CT, an X-ray beam emitted from an X-ray tube is collimated into a fan shape to be passed or penetrated through a subject so as to resultantly attain information of attenuation thereof. The attenuation information is attained by an X-ray sensor disposed behind the subject. While keeping the relative position of the X-ray beam with respect to the X-ray sensor, the beam emitter is turned about an axis of the subject. Attained information is processed by a computer of the tomograph to produce or reconstruct an X-ray tomogram.

To process images at a high speed, there is employed a multi-channel X-ray sensor in which a plurality of X-ray sensing elements are ordinarily arranged in a circular arc with an X-ray tube disposed at a focal point thereof.

In this connection, when the X-ray beam enters the subject, the beam is not only absorbed by textures or tissues to be thus attenuated but also subjected to scattering due to interaction with atoms constituting the tissues. As known, the X-ray scattering is classified into the Rayleigh scattering related to a phenomenon of interference and the Compton scattering not related thereto.

(1) Rayeigh scattering

When a photon of the X-ray passes a position in the neighborhood of an electron, the electron is caused to vibrate according to an electric field formed by the photon to resultantly absorb the photon such that the electron radiates a photon having the original oscillation frequency. In consequence, the scattered X-ray has a wavelength equal to that of the incident X-ray, leading to interference between the incident and scattered X-rays. Probability of occurrence of the Rayleigh scattering associated with the interference is smaller than that of the Compton scattering. However, the Rayleigh scattering is characterized by sharp scattering of particles toward the front side of scattering. In a case where X-ray having low energy is incident to a substance having a large atomic number, the scattered rays resultant from the Rayleigh scattering take a large part in the overall scattered rays.

(2) Compton scattering

When a photon of the X-ray collides with a free electron of a substance or an electron on an outer orbit of an atom weakly linked with a kernel thereof, the collided electron cannot absorb the entire energy of the photon and hence emits a portion of the energy in the form of a photon. As a result, the electron is emitted according to the remaining kinetic energy. This phenomenon is called Compton effect. In regard to the incident photon, the photon re-emitted by transforming the energy and the photon emitted due to the collision are called Scattered photon (X-ray) and Compton electron, respectively. When the energy of the incident X-ray becomes higher, the ratio of the Compton scattering is increased in the overall scattering.

(3) Influence of scattered X-ray on image

Each of the sensing elements measures attenuation of the X-ray in a portion of the subject on a line (measuring path) drawn between the focal point of the X-ray tube and the center of the sensing element. When there exist scattered X-rays from other portions of the subject, an error appears in measured values. The scattered X-rays incident to the element increase the output therefrom and hence X-ray attenuation through the portion of the subject in the measuring path is virtually decreased in the data resultant from measurement. When the error becomes greater, there occurs deterioration in resolution of a CT image produced from the measured data. Particularly problematic is reduction in low-contrast resolution called density resolution. Additionally, there clinically exists a rib archifact in which the CT value is virtually decreased for the inside of ribs and hence a dark zone resultantly appears in the obtained image or picture. Moreover, there possibly exists a case in which the CT value varies between various positions in the liver. Consequently, to attain an accurate X-ray tomogram, it is necessary to remove influence of scattered X-rays.

The known methods of removing influence of scattered X-rays are as follows.

(1) Scattered X-rays are prevented from entering an X-ray sensing surface of each channel of the X-ray sensor.

(2) The output component caused by the pertinent scattered X-rays is subtracted from each channel output of the X-ray sensor.

As a specific method of the procedure (1) above, there have been proposed provision of a grid parallel to the X-ray sensing surface of each channel (described in, for example, the JP-A-62-60539 and JP-A-4-336044) and arrangement of a filter in front of the sensing surface (described in, for example, JP-A-62-270137).

The procedure (2) is in general achieved as follows. Namely, the quantity of scattered X-rays is actually measured so as to subtract the obtained value from the output of each channel. There has been proposed a configuration in which a plurality of scattered X-ray sensors are disposed to sense scattered-X-ray in front of a main X-ray sensor (described in, for example, JP-A-63-305846, JP-A-63-38438, JP-A-63-40534, and JP-A-1(64)-62126). Moreover, there has been proposed a method in which the X-ray sensor includes only a main sensor such that a rod made of lead is arranged to absorb X-rays in front of each channel so as to remove only X-rays which serve as a signal in the actual measurement (as described in, for example, JP-A-62-261342).

(3) In addition, another specific method of the procedure (2) has been described in the JP-A-4-170942.

In this method, there are prepared scattered X-ray correction constants including an air correction constant calculated from a regression line $y=ax+b$ associated with the total channel data value for a first rotary angle and a correction constant related to a water phantom. In the actual case, after all measured data values (for air calibration, phantom calibration, and subject measurement) are converted into the logarithmic expression and then are multiplied by correction coefficients after the logarithmic conversion. Namely, the correction is conducted after the measured data are converted into the logarithms expression.

According to the prior art described above, when the measurement is achieved using the procedure (1) to remove X-rays entering the sensor, the incident intensity of the signal X-rays is also lowered and hence the signal-to-noise (S/N) ratio is deteriorated. This accordingly leads to a problem of an unsatisfactory CT image. On the other hand, in association with the procedure (2) to actually measured scattered X-rays so as to remove the quantity thereof from the data, the method using a sensor dedicated to scattered X-rays is attended with the following problem.

The scattered X-ray sensor arranged in front of the main X-ray sensor increases thickness of the overall body of X-ray sensor, leading to difficulty in mounting the sensor for measurement. To solve the problem, there has been known a method in which a scattered X-ray sensor of a small size is disposed to be adjacent to the main X-ray sensor in a channel slicing direction at the central portion of the main X-ray sensor so as to measure the quantity of scattered X-rays in the central portion. The quantity of scattered X-rays in each channel in the peripheral portion is obtained through calculation according to an expansion function.

However, between the main sensor (usually having structure like that of an ionization chamber) and the scattered X-ray sensor (ordinarily having constitution like that of a solid state sensor), there appears a discrepancy in scattered X-ray sensitivity due to structural difference therebetween. Consequently, this configuration is not advantageous for practices.

Furthermore, the construction including the scattered X-ray sensor in addition to the main X-ray sensor requires the expensive sensor and sensing circuit to be duplicated. This considerably increases the cost thereof in any case where the scattered X-ray sensor is in front of or adjacent to the main sensor.

On the other hand, according to the procedure (2), in the method in which only the main X-ray sensor is used so as to employ a shielding device to remove signal X-rays when measuring scattered X-rays, a complex function is additionally required to operate the apparatus while keeping the positional accuracy of the shielding device. This inevitably leads to increase in the cost of the system.

(a) It is necessary to execute processing to obtain scattering constants Ca, Cw, and Cs so as to estimate the content of scattered rays in the measured data, scattering correction processing for water phantom data according to the scattering constants Ca and Cw and other data, and scattering correction processing for raw data according to the scattering constants Ca and Cs and other data. This consequently increases the amount of processing and the load imposed on the computer.

(b) Although the various processing of (a) may possibly remove the influence of scattered rays, there exist quite complicated relationships between occurrence and influence of scattered rays and some of such relationships are independent of the internal constitution of the subject. In consequence, the above correction method corresponding to the measured values (proportional to attenuation of rays) is not sufficient to completely correct influence of the scattered rays.

SUMMARY OF THE INVENTION

It is therefore an object of the present invention to provide a method of and an apparatus for correcting scattered X-rays for use in an X-ray computerized tomograph capable of exactly calculating the total quantity of scattered rays and achieving a high-precision correction of scattered X-rays without soaring the cost thereof and a multichannel X-ray sensor capable of efficiently sensing the scattered rays.

The principle of the present invention will be first described.

The following relationship exists between the intensity of an X-ray incident to a subject and that of the X-ray passed therethrough.

$$I = I_0 \exp(-\mu x)$$

where, I indicates the intensity of the X-ray after passing through the subject, $I_0$ stands for the intensity of the X-ray incident to the subject, $\mu$ designates the attenuation coefficient depending on the subject, and x represents the thickness of the subject.

In general, to obtain a CT image, namely, a computerized tomogram, the value of $\mu x$ is first obtained to configure a picture therefrom. For this purpose, measured data is transformed into logarithms to extract $\mu x$ as data for image processing.

On the other hand, the value of scattered rays (s) is incorporated in the form of addition as $I_0 \exp(\mu x) + s$. Since the value of the scattered rays (s) cannot be obtained from the data converted into logarithms in the conventional fashion, the scattered rays (s) cannot be appropriately corrected. To achieve a satisfactory correction of the scattered rays (s), it is necessary to use the values in a linear region in which the values before the transformation, namely, the scattered rays and absorbed X-rays are represented in the form of addition as above. The linear region represents a state before the logrithms conversion. Description will now be given of specific examples of a method of and an apparatus for correcting scattered rays in accordance with the present invention.

According to the present invention, measured values of X-rays are subjected to a logarithmic conversion. Based on the transformed data, the amount of scattered X-ray correction is obtained in the linear zone or region. The converted data is then subjected to an inverse logarithmic transformation so as to attain a value in the linear zone. The amount of scattered X-ray correction is subtracted from the resultant value, thereby achieving the scattered X-ray correction.

Furthermore, according to the present invention, measured X-ray values are subjected to a logarithmic conversion. Based on the transformed data, there are obtained parameters representing a contour of the overall subject. From the parameters, the amount of scattered X-ray correction is obtained in the linear zone. The converted data is then subjected to an inverse logarithmic transformation so as to attain a value in the linear region. The amount of scattered X-ray correction is subtracted from the resultant value, thereby achieving the scattered X-ray correction.

The parameters include a total or accumulated value, a mean value, and a variance of output values from a plurality of channels at predetermined positions of the sensor.

According to the present invention, there is provided an X-ray computerized tomograph in which the measured data undergone the correction in the above correction method is subjected to a logarithmic conversion so as to produce an image or a tomogram from the obtained data.

To achieve the method above, there is provided an X-ray computerized tomograph in accordance with the present invention including a memory for storing therein a correction function $y = f(x)$ representing a relationship between the total channel accumulation value x attained by adding to each other measured values which are resultant from measurement of phantoms having different diameters and which are subjected to various logarithmic conversions for a particular rotary angle of the sensing system and the amount y of scattered X-ray correction, a circuit for carrying out a logarithmic transform for measured data $D_{ij}$ obtained by measuring the subject while changing the rotary angle (i indicates a rotary angle number; i=1, 2, ..., m; j stands for a channel number; j=1, 2, ..., n), a circuit for processing the measured data $D(LG)_{ij}$ after the logarithmic conversion to obtain the total or accumulation value $x_k$ of X-ray data after the logarithmic conversion of each channel for an arbitrary rotary angle, a circuit for accessing the memory according to the total channel accumulation value $x_k$ to obtain the amount $y_k=f(x_k)$ of scattered ray correction in the associated linear region, a scattered X-ray correction circuit for achieving an inverse logarithmic conversion for the measured data $D(LG)_{ij}$ (i=1, 2, ..., m; j=1, 2, ..., n) undergone the logarithmic conversion to attain the original data $D(LN)_{ij}$ in the linear region so as to subtract the amount $y_k$ from $D(LN)_{ij}$, and a circuit for again conducting a logarithmic conversion for each of the resultant data $D(LN)_{ij}-y_k$ (i=1, 2, ..., m; j=1, 2, ..., n) to construct an image according to the obtained data.

The function $y=f(x)$ is a function of power, an exponential function, a broken-line function, or a step-formed function.

In addition, the phantom has a cylindrical shape and its tomogram is hence of a circular contour, whereas a human body has in general a tomogram having an elliptic form. As a result, for the outputs obtained via a plurality of channels in the central portion of the multichannel X-ray sensor, the attenuation through a human body is smaller than that through a phantom. The outputs take consequently higher values in the case of the human body. This means that the amount of correction for the human body is required to be greater than that of the phantom obtained from the correction curve. In addition, while the phantom is made of a uniform material, the human body is a set of mutually different members such as bones and entrails and hence has a correction curve having an inclination or a gradient different from that of the phantom. To solve the problem of discrimination of the subject, according to the present invention, a phantom is discriminated from a human body by measuring outputs from a plurality of channels in the central portion of the multichannel X-ray sensor. When the subject is a human being, correction coefficients or a correction curve preset according to data of humans are or is adopted to correct the scattered X-rays. This enables the scattered X-ray correction with a high precision.

To achieve the method above, there is provided an X-ray computerized tomograph according to the present invention including a memory for storing therein a correction function $y=f(x)$ representing a relationship between the total channel accumulation value x attained by adding each measured value which is resultant from the phantom measurement for each diameter and which is subjected to various logarithmic conversions for a particular rotary angle of the sensing system and the amount y of scattered X-ray correction, a function $A'=h(x)$ representing a relationship between the total channel accumulation value x and the mean value (alternatively, the accumulation value or variance) $A'$ of data from a plurality of channels including a central channel of the X-ray sensor, and a threshold value function $A=g(x)$ which is positionally higher than the function $A'$ and which is used to identify whether or not the contour of the subject is similar to that of the phantom, a circuit for carrying out a logarithmic transform for measured data $D_{ij}$ obtained by measuring the subject while changing the rotary angle (i indicates a rotary angle number; i=1, 2, ..., m; j stands for a channel number; j=1, 2, ..., n), a circuit for processing the measured data $D(LG)_{ij}$ after the logarithmic conversion to obtain the total $x_k$ of X-ray data after the logarithmic conversion of each channel for an arbitrary rotary angle and the mean value (alternatively, the total value or variance) $B_k$ of data related to a plurality of channels including the central channel of the X-ray sensor, a circuit for accessing the memory according to the total channel value $x_k$ to obtain according to the above three functions the amount $y_k=f(x_k)$ of scattered ray correction, the mean value (alternatively, the total value or variance) $A'_k=h(x_k)$, and the threshold value $A_k=g(x_k)$ in the associated linear region, a circuit for comparing $B_k$ with $A_k$ to correct when $B_k$ is larger than $A_k$ the amount of scattered X-ray correction in the linear region to attain a corrected amount scattered X-ray correction and to output therefrom when $B_k$ is smaller or equal to $A_k$ the amount $y_k$ without modification thereof, a scattered X-ray correction circuit for achieving an inverse logarithmic conversion for the measured data $D(LG)ij$ (i=1, 2, ..., m; j=1, 2, ..., n) undergone the logarithmic conversion to attain the original data $D(LN)_{ij}$ in the linear zone so as to subtract the amount $y_k$ or $y'_k$ from $D(LN)_{ij}$, and a circuit for again conducting a logarithmic conversion for each of the resultant data $D(LN)_{ij}-y_k$ or $D(LN)_{ij}-y_k'$ (i=1, 2, m; j=1, 2, ..., n) to construct an image according to the obtained correction data.

Furthermore, according to the present invention, there is provided a multichannel X-ray sensor for an X-ray computerized tomograph in which the sensor is disposed opposing to an X-ray source and which includes an X-ray sensing area equal to or more than an area covered by a fan beam angle of X-rays from the X-ray source, thereby sensing scattered X-rays in an X-ray sensing area beyond the area associated with the fan beam angle.

Additionally, the X-ray sensing area beyond the fan beam angle includes an X-ray sensitive area oriented toward the center of the scanner opening.

Moreover, the X-ray sensing area beyond the fan beam angle includes an X-ray sensing width larger than that of each channel in the fan beam angle in the channel direction of the X-ray sensor.

According to the present invention, there is provided a multichannel X-ray sensor disposed opposing to an X-ray source in which an X-ray beam width vertical to the channel arranging direction is controlled by a collimator to be equal to or less than the width of the slit-shaped X-ray sensing surface. The X-ray sensor has an X-ray beam receiving position which can be changed over between a position in the X-ray sensing surface (in the measuring mode) and a position beyond the X-ray sensing surface (in the scattered X-ray measuring mode). Thanks to the provision, when the beam receiving position is beyond the X-ray sensing surface, X-rays incident to the X-ray sensing surface is sensed as scattered X-rays.

As described above, in accordance with the present invention, the amount of scattered X-rays is detected only by an X-ray sensor including a main X-ray sensor of a single kind so that influence of scattered X-rays is corrected prior to producing an X-ray image. Consequently, a high-quality computerized tomogram can be favorably attained without increasing cost and size of the X-ray computerized tomography.

BRIEF DESCRIPTION OF THE DRAWINGS

These and other objects and advantages of the present invention will become apparent by reference to the following description and accompanying drawings wherein:

FIGS. 18A to 18C are diagram showing various embodiments in which the X-ray receiving position is altered in FIG. 17.

DESCRIPTION OF THE PREFERRED EMBODIMENTS

Figure 1:
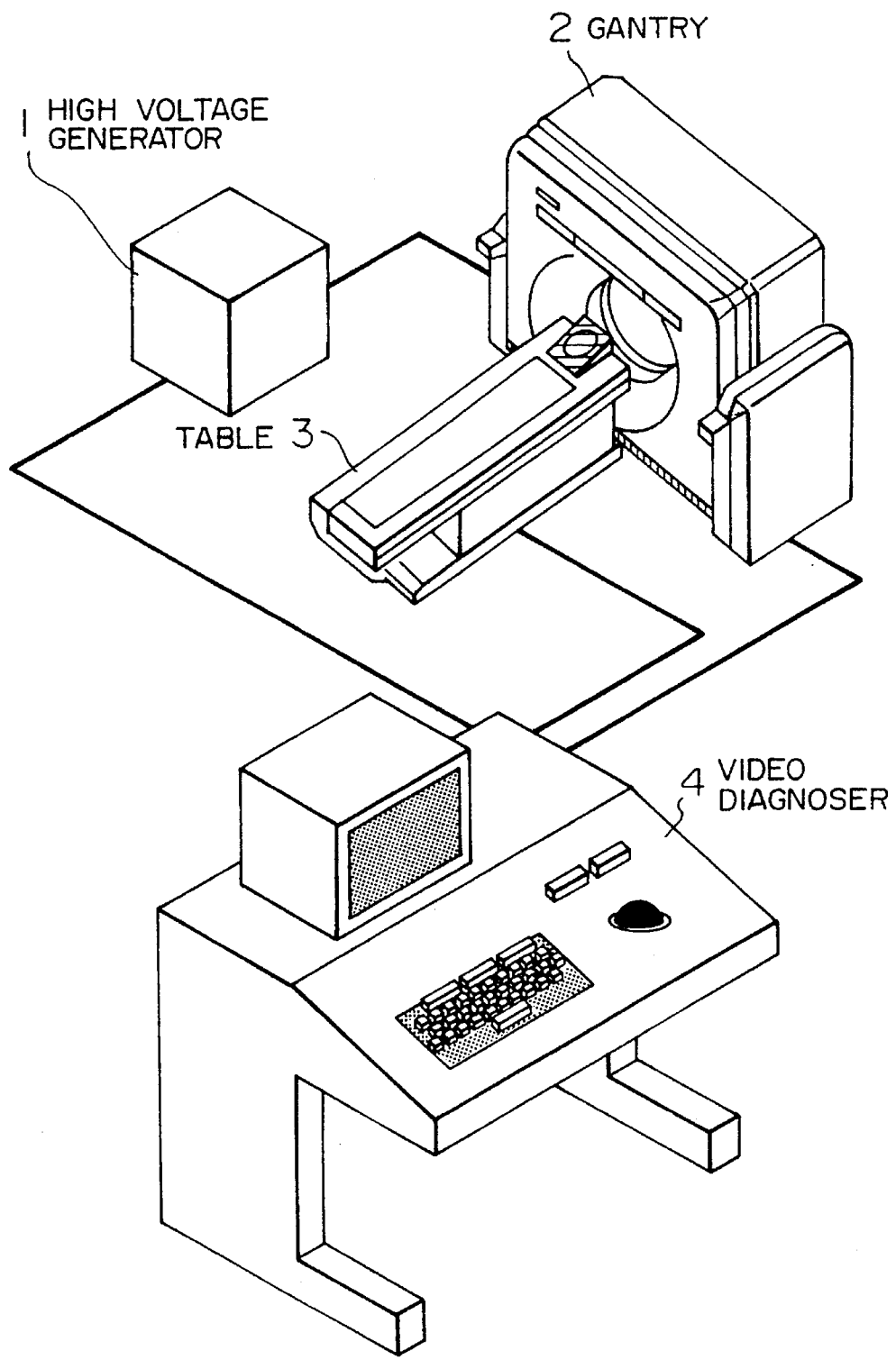
FIG. 1 is a diagram showing an appearance of an X-ray computerized tomograph to which the present invention is applied.

FIG. 1 shows an outline of the primary portion of an X-ray CT to which the present invention is applied. In this diagram, a high voltage generator 1 is disposed to generate X-rays by an X-ray tube, not shown, arranged in a gantry 2. In the gantry 2, there is disposed an X-ray radiating apparatus including an X-ray tube and a collimator and a multichannel X-ray sensor, not shown, disposed to oppose each other with a circular hole therebetween. The hole is used to locate a predetermined portion of a subject (patient) at a desired position. These two constituent apparatuses rotate with the opposing state kept unchanged. The subject is mounted on a table 3 to be transported by a conveying facility, not shown, to a predetermined position in the hole of the gantry 2. A video diagnoser 4 includes a central control unit and a data processing unit of the X-ray CT having an integrated computer. The diagnoser 4 also accomplishes data processing to remove influence of scattered X-rays.

Figure 2:
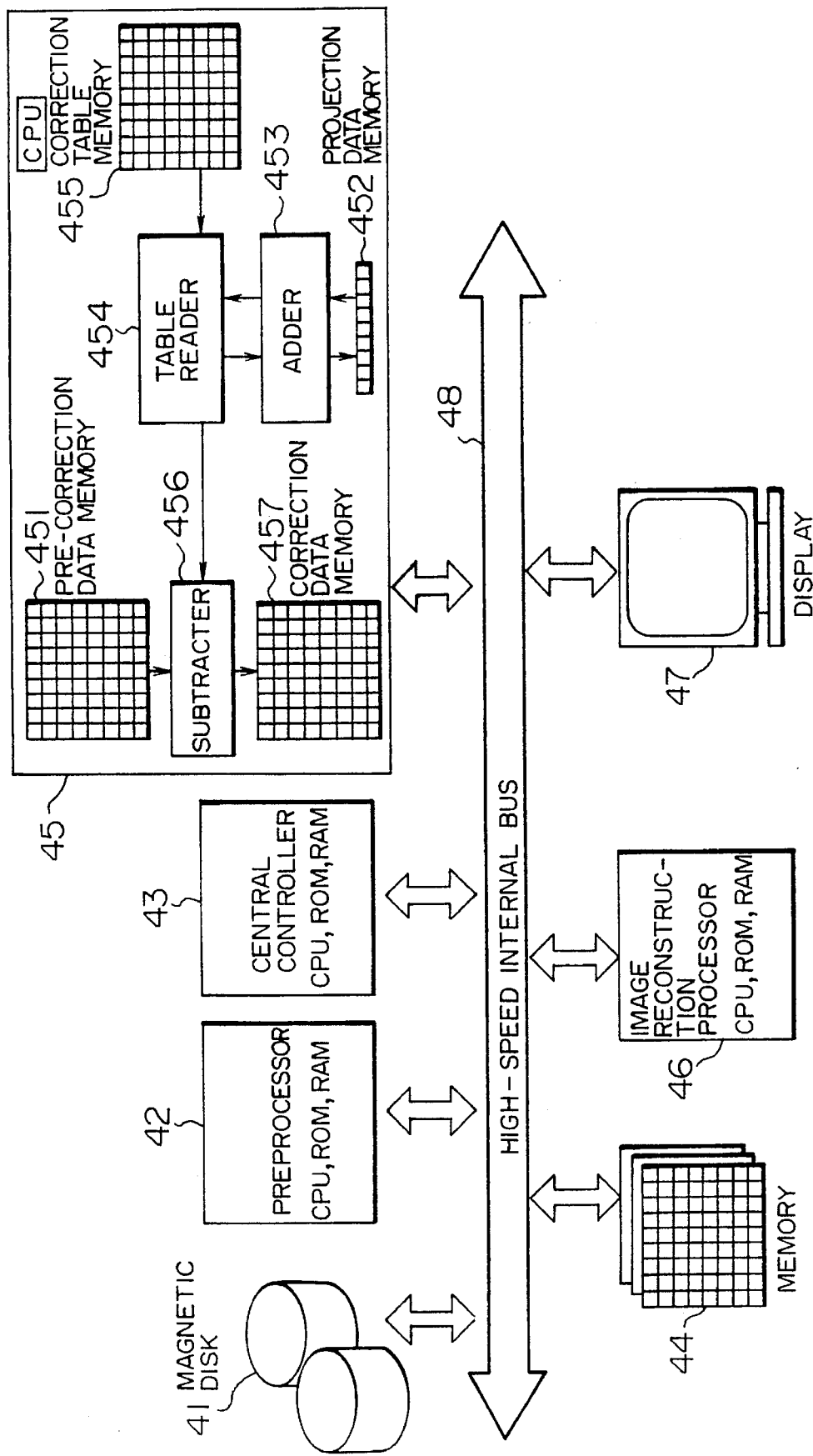
FIG. 2 is a schematic diagram showing an embodiment of a video diagnoser using an X-ray computerized tomograph according to the present invention.

FIG. 2 shows the main constituent elements of the video diagnoser 4.

In this diagram, the diagnoser 4 includes the following components.

Magnetic disk 41:

The disk 41 is disposed to store measured data and CT image data attained by the X-ray sensor.

Preprocessor 42:

The preprocessor 42 includes a central processing unit (CPU), a read-only memory (ROM), and a random access memory (RAM) to execute various preprocessing such as sensitivity correction and algorithmic transform. The preprocessor 42 computes the total channel value, that is the added value of values of all channels undergone the logarithmic transform.

Central controller 43:

The controller 43 includes a CPU, an ROM, and an RAM to conduct sequence controls for mechanical and electrical systems of the X-ray CT. For the mechanical system, there is achieved rotation control for the X-ray source and the X-ray sensor with respect to the opposing relationship therebetween. For the electrical system, there is conducted operation, for example, to control generation of X-rays and to control collection timing of measured signals.

Main memory 44:

The main memory 44 is used to store such programs as operating systems and sequence control programs and various work data for the image or video processing.

Scattered ray correcting section 45:

The section 45 is an essential part of the embodiment to effect scattered ray correction for measured data (including measured data undergone sensitivity correction or the like) from the magnetic disk 41 and the main memory 44. For the correction, the section 45 includes a pre-correction data memory 451, a projection data memory 452, an adder 453, a table reader 454, a correction table memory 455, a subtracter 456, and a correction data memory 457. The correction processing is controlled by the CPU.

Image reconstruction processor 46:

The processor 46 includes a CPU, an ROM, and an RAM to reconstruct an image according to data undergone a scattered ray correction by the correcting section 45.

Display 47:

The display 47 presents thereon such pictures as a computerized tomogram thus produced.

Common bus 48:

The bus 48 transfers data between the constituent components.

Figure 3:
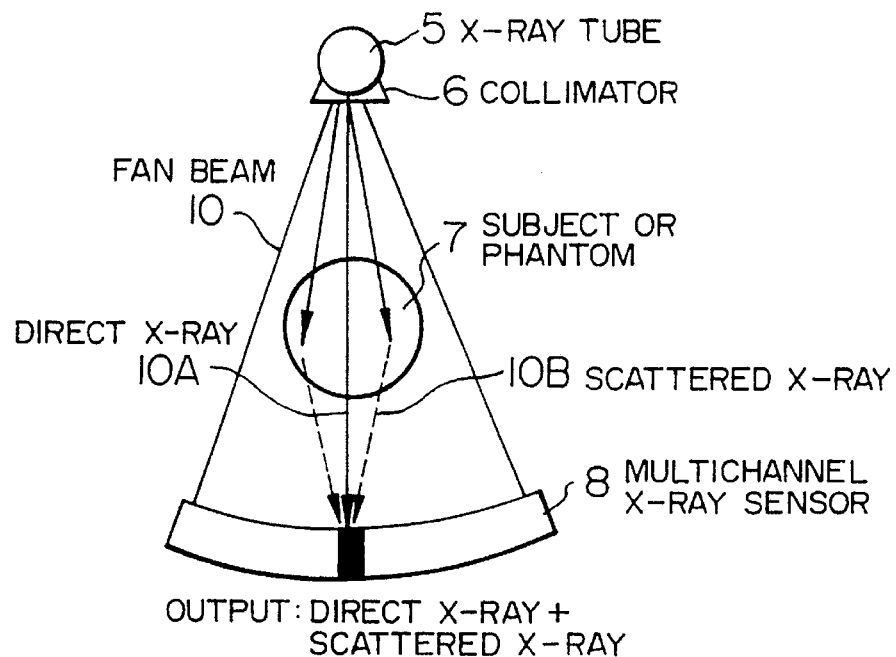
FIG. 3 is a diagram showing an arrangement an X-ray sensor in an embodiment according to the present invention.

FIG. 3 shows operation of measuring rays by a main X-ray sensor as an embodiment according to the present invention. In operation, an X-ray beam produced from an X-ray tube 5 is collected by a collimator 6 into a fan beam 10. The fan beam X-ray 10 enters a subject or phantom (scattering body) 7 in a measuring space. The beam 10 passes through the body 7 while intensity thereof is being attenuated. A direct X-ray 10A containing useful X-ray information is incident as a signal X-ray to an X-ray sensor 8 arranged on the rear side of the subject or phantom 7 along a circular arc with a center thereof set to a focal point of the X-ray tube.

On the other hand, scattered X-rays from the body 7 possibly enter X-ray sensing elements of the same channel as shown in the diagram. As a result, for this channel, there is produced an output related to the direct X-ray and the scattered X-ray.

the phantom or subject is used for measurement of the amount of scattered ray correction and measurement of a computerized tomogram of the subject, respectively. Namely, when obtaining the correction amount or the tomogram, the phantom or subject is mounted on the table, respectively.

Figure 4:
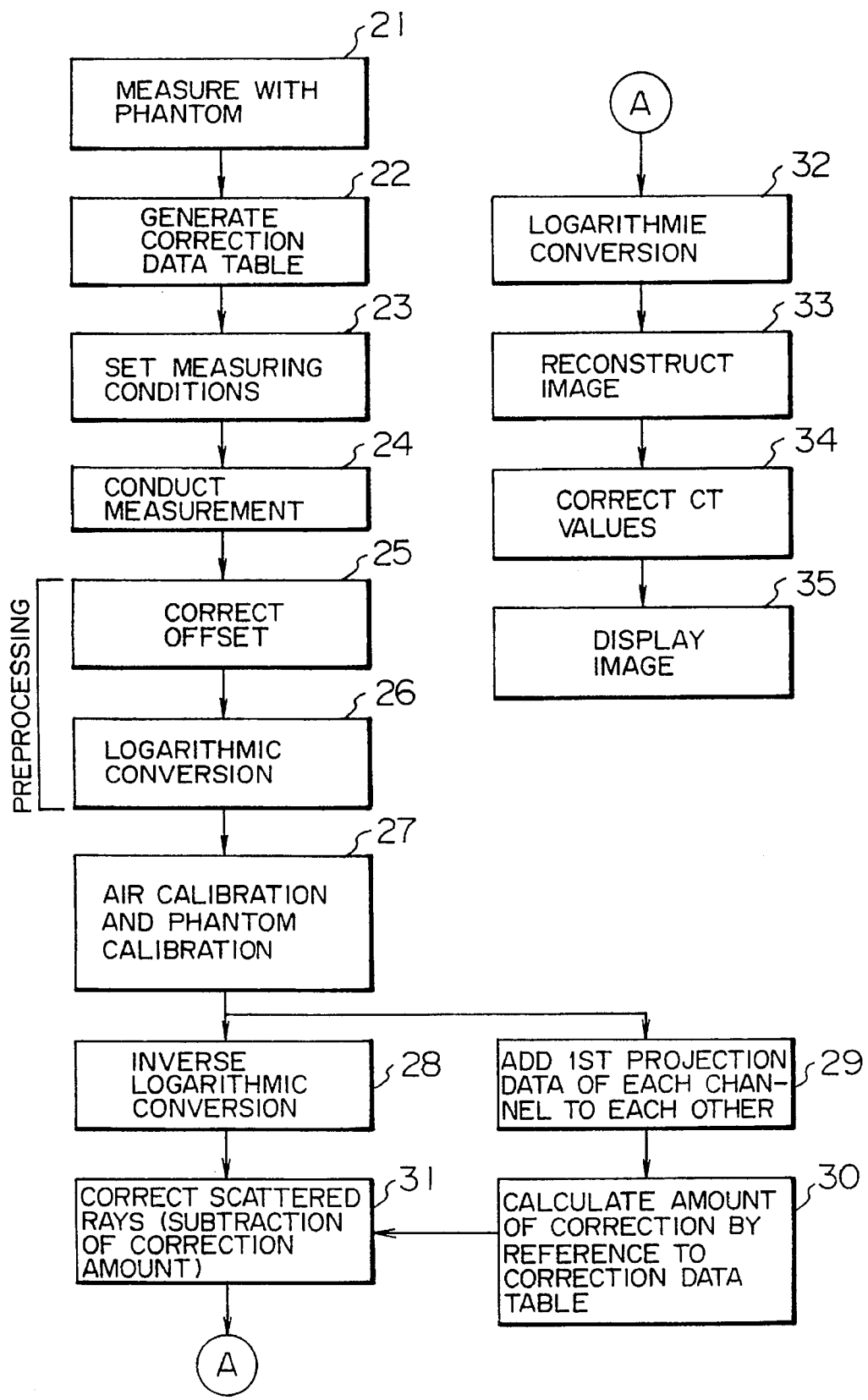
FIG. 4 is a flowchart showing video processing in the X-ray CT according to the present invention.

FIG. 4 is a flowchart showing the procedure of processing an X-ray tomogram by the video diagnoser 4.

Before measurement is conducted with a subject for a computerized tomogram, a phantom made of a uniform substance is measured to attain the amount of correction for phantom calibration so as to correct variations in the characteristic between the sensor elements (step 21). Based on measured values of the phantom, there are manually or automatically obtained a correction amount for the phantom calibration and an amount of scattered ray correction. The obtained values are stored in the memory 44 of FIG. 2. According to the amount of scattered ray correction, a scattered ray correction curve representing a relationship between the measured data undergone the logarithmic conversion and the amount of scattered ray correction is produced in the form of a correction data table in the memory 44 (step 22). Data stored in the memory 44 is read into the correction table memory 455 when necessary for calculation of the amount of scattered ray correction. The procedure to obtain the scattered ray correction curve will be described later.

To obtain a computer tomogram, measurement of the subject is carried out as follows.

First, the subject is mounted such that a predetermined portion of the subject is placed at the measuring position in the gantry 2 and then measuring conditions to gather penetrated X-ray data are inputted from a keyboard of the video diagnoser 4 (step 23). Next, an X-ray beam is radiated according to the conditions to measure intensity of X-rays passed through the subject 7 by the multichannel X-ray sensor (step 24).

After data of X-rays from the subject 7 is measured, there is conducted a preprocessing process for data correction. The preprocessing includes processing of offset correction (step 25) and logarithmic conversion (step 26). The preprocessing is executed in the preprocessor 42 such that data resultant from the processing is saved on the magnetic disk 41.

In the offset correction (step 25), variations in characteristics are corrected between the respective channels of the X-ray sensor 8.

As for the logarithmic conversion (step 26), since the intensity of X-rays passing through the subject 7 is attenuated in a manner like an exponential function, a logarithmic conversion is accomplished for an X-ray intensity ($D_{ij}$; i indicates a rotary angle number; i=1, 2, 3, ..., m; j denotes a channel number; j=1, 2, 3, ..., n) obtained by the sensor 8, thereby producing projection data ($D(LG)_{ij}$) to display an image.

The measured data after the preprocessing (projection data; data undergone the preprocessing is called measured data) is subjected to a calibration (step 27) to conduct an air calibration or a phantom calibration for sensitivity correction. This process compensates for nonlinearity of attenuation of each channel of the X-ray sensor 8. Namely, the sensitivity to an X-ray incident to the sensor 8 varies between the channels and hence the voltage outputted from a preamplifier also varies therebetween even under the same condition. The sensitivity discrepancy between the channels of the sensor 8 is corrected according to values obtained by the air or phantom measurement for the respective channels. Through the above process, the sensitivity difference and nonlinearity due to variations between the channels of the sensor 8 are completely calibrated.

Subsequently, data of scattered X-rays is removed from the X-ray data.

First, the X-ray data in the logarithmic expression (undergone the channel correction; $D(LG)_{ij}$) is subjected to an inverse logarithmic conversion to resultantly create data $D(LN)_{ij}$ (step 28). The produced data $D(LN)_{ij}$ is restored to data before the logarithmic conversion (specifically, to data undergone the preprocessing and calibration). The obtained data is called "data in the linear region". The reason for adoption of the data in the linear region resides in that the scattered ray correction is achieved in the linear region in which processing of subtraction is possible. The scattered ray correction in the linear region leads to an advantage that the amount of scattered ray correction is increased in such a locally existing portion of the subject as a bone associated with a high X-ray attenuation so as to improve the phenomenon in which the calculated CT values around the bone disadvantageously become smaller than the actual values due to the scattered rays.

To conduct the scattered ray correction in the linear region, the amount of scattered ray correction is required to take values in the linear region. For the correction amount, there is employed the total channel accumulation value undergone the logarithmic conversion. Assume this value to be expressed as x. First, a relationship y=f(x) is determined between various values of x from phantoms having different sizes and the values of amount of scattered ray correction y obtained in the linear region. According to the function y=f(x), there is attained a relationship $y_k=f(x_k)$ of the amount of scattered ray correction $y_k$ with respect to the total channel accumulation value $x_k$ obtained from the actual subject and undergone the logarithmic conversion.

In this connection, the total channel accumulation value x may be selected as a value before or after the logarithmic conversion or a value undergone the inverse logarithmic conversion (each being in the linear region). This embodiment uses the value after the logarithmic conversion for the following reasons.

(1) A fact that the total amount of scattered rays is determined in association with the size of the subject can be confirmed through experiments. The size of subject does not indicate that of an area of the slice surface thereof, but denotes that of total amount of X-rays obtained via the slice surface. The total amount of X-rays stands for the value after the logarithmic conversion. Namely, the amount includes neither the value before the logarithmic conversion nor the value after the inverse logarithmic conversion (each in the linear region), which will be described in Article (3) later.

(2) To obtain an appropriate amount of scattered ray correction according to the subject, it is necessary to estimate the size thereof. For this purpose, the total channel value which is obtained by adding values of all channels is appropriately utilized.

(3) Scattered X-rays are correctly reflected not in the total channel value in the linear region but in the total channel value after the logarithmic conversion. That is, in the measurement of data in the linear region, when the X-rays are considerably attenuated, namely, when the subject is made of a substance through which X-rays are not easily passed or which has a large size, the ratio of scattered rays to the primary rays becomes higher. However, the total channel value becomes smaller. Conversely, when the attenuation is small, namely, when the subject is made of a substance through which X-rays are easily transferred or which has a small size, the ratio of scattered rays to the primary rays is decreased. However, the total channel value is increased. In consequence, the magnitude of the total channel accumulation value in the linear region develops a relationship opposite to that of the scattered X-rays, namely, the scattered X-rays are not appropriately reflected therein. Consequently, the total channel accumulation value cannot be used to estimate the size of the subject. On the other hand, in the value after the logarithmic conversion having a relationship reverse to that of the data in the linear region, the scattered X-rays are not appropriately reflected.

Figure 5A:
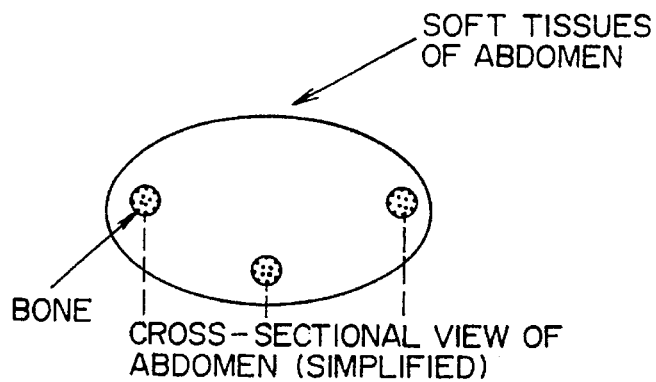
FIGS. 5A to 5D are diagrams for explaining scattered ray correction in an abdomen model.
Figure 5B:
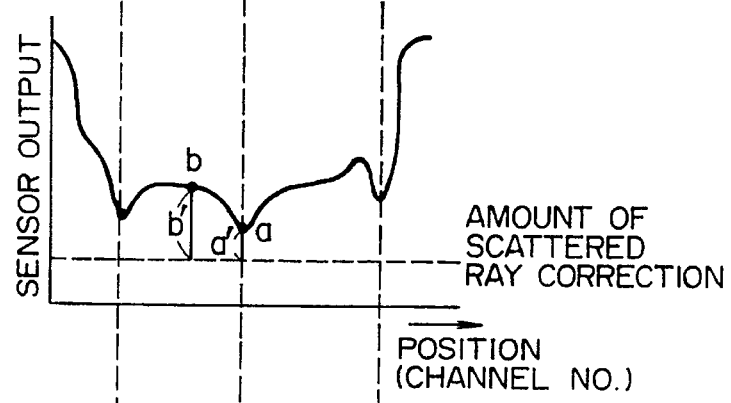
Figure 5C:
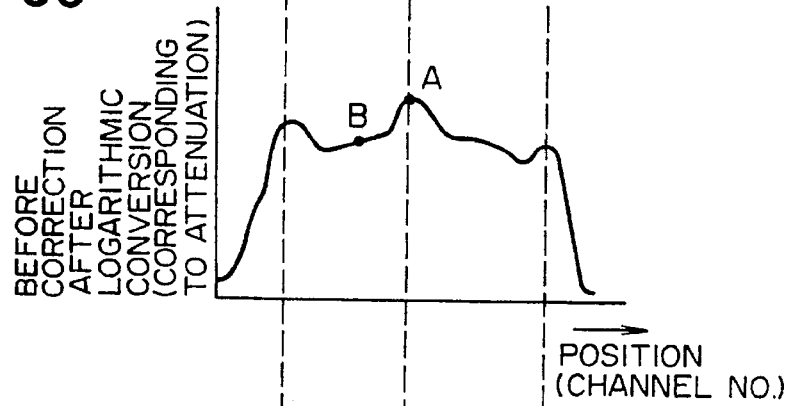
Figure 5D:
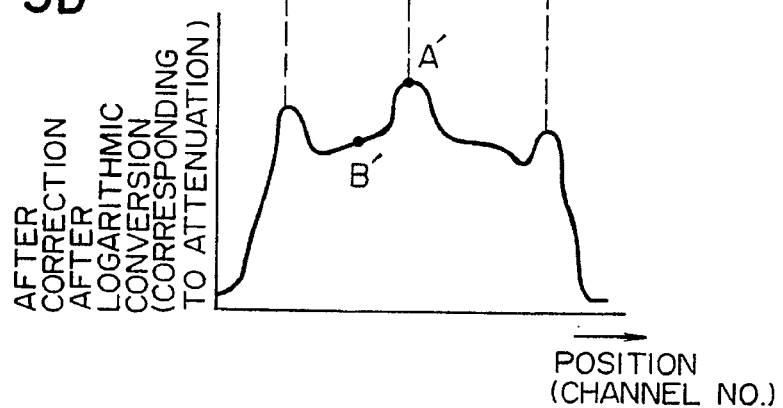

FIGS. 5A to 5D and FIG. 6 show the relationships described above. FIG. 5A shows by way of example an abdomen model in which soft tissues occupy most portions thereof with three bones therein. FIG. 5B is a graph showing outputs sensed for the tissues of FIG. 5A in which the abscissa denotes the position of the subject (equivalent to the channel number) and the ordinate designates sense values via the respective channels. The output values are decreased for positions of bones, indicating that the X-ray attenuation is large in these positions. According to the present invention, a fixed amount of scattered ray correction is subtracted from the data of each channel. FIG. 5C shows data after the logarithmic conversion in relation to the data of FIG. 5B. FIG. 5D shows data after the scattered X-ray correction. In FIGS. 5B to 5D, correspondences are established between points a, A, and A' and between points b, B, and B'.

The influence of scattered rays is exerted such that the difference in the plotted data is minimized between the bones and the soft issues. With the influence kept unchanged, the data is obtained as shown in FIG. 5C. Thanks to the scattered ray correction according to the present invention, the data difference can be clarified or magnified between the bones and the soft tissues as shown in FIG. 5D.

Figure 6:
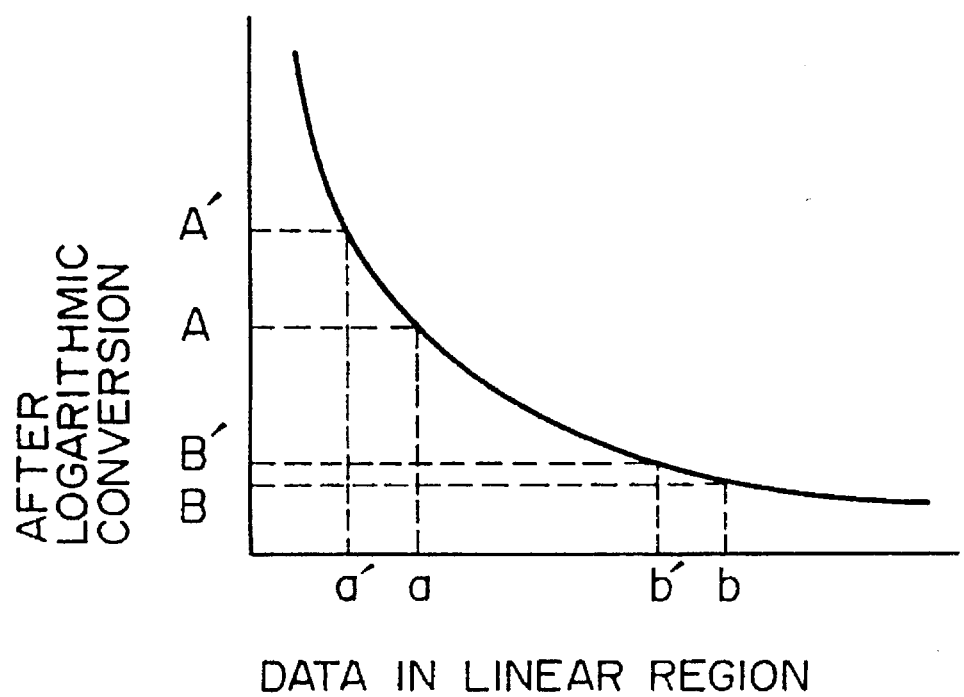
FIG. 6 is a diagram for explaining scattered ray correction according to a logarithmic conversion table.

FIG. 6 shows a logarithmic conversion table for use in logarithmic conversion. As can be seen from this table, the order of values of data items in the linear region are reversed after the logarithmic conversion. Moreover, the scattered ray correction is applicable to an identical for all channels value without any problem.

The abscissa indicates data in the linear region and the ordinate denotes data undergone the logarithmic conversion. Letters a and b stand for data items before correction shown in FIG. 5B, whereas a' and b' represent data after correction. In FIG. 6, the discrepancy between the data items a and a' is assumed to be equal to that between the data items b and b'. For these data items at four points, as a result of the logarithmic conversion, there is obtained a relationship of (A'–A)>(B'–B) for the difference A'–A between the associated data items A' and A after the logarithmic conversion and the difference B'–B between the corresponding data items B' and B after the conversion. That is, thanks to subtraction of the fixed correction amount, for two pairs of data items of which the difference therebetween is identical to each other in the linear region, there is obtained the following relationship after the data items are subjected to the logarithmic conversion. The smaller the linear value is, the greater the value and the increase ratio thereof are. Conversely, the greater the linear value is, the smaller the value and the increase ratio thereof are. This facilitates clear distinction between the soft tissue and, the bone.

Returning to FIG. 4, from the measured data after the calibration (step 27), there is calculated the total channel accumulation value (step 29). This total channel value is obtained by adding to each other the respective channel value after the logarithmic conversion. Obtained from this value is an appropriate correction amount for the scattered X-rays in the linear region. In FIG. 4, however, the total channel value is not obtained for an arbitrary rotary angle of the sensing system. Namely, the value is produced by adding to each other the projection output data items related to the respective channels at a first rotary position (for example, at a position of rotary angle=0°) for the X-ray data after correction. The adding operation of the data items is accomplished by the correction processor 45.

Although the total channel accumulation value can be decided from data items associated with one rotary angle, since the computerized tomograph achieves the processing of measured data immediately after measurement thereof, it is favorable to use data first obtained immediately after the measuring step is initiated.

In the pre-correction data memory 451 of the correction processor 45 (FIG. 2), there is stored X-ray data $D(LG)_{ij}$ undergone the logarithmic conversion (undergone the pre-processing and calibration). Of the data, projection data items related to n channels at the first rotary position $D(LG)_{11}, D(LG)_{12}, D(LG)_{13}, \ldots, D(LG)_{1j}$, and $D(LG)_{1n}$ are stored in the projection data memory 452. In this connection, although the first rotary position is set as θ=0°, there may be arbitrarily specified a particular projection position for angle θ=α°. After the data at the first rotary position is stored in the memory 452, all data of the memory 451 is subjected to an inverse logarithmic conversion. Alternatively, the data undergone the inverse logarithmic conversion may be initially stored in the memory 451, whereas there may be stored in the memory 452 the data of all channels at the first rotary position after the logarithmic conversion.

In the adder 453, the projection data items of n channels from the memory 452 are added to each other to obtain the total channel accumulation value as follows (step 29).

$$x_k = \sum_{j=1}^{D} D(LG)_{ij} \tag{1}$$

The total channel value $x_k$ is produced by adding to each other data items of all channels after the logarithmic conversion. The value $x_k$ is supplied to the table reader 454. According to a scattered X-ray correction curve stored in the correction table memory 455, there is obtained a value $y_k$ corresponding to the value $x_k$, namely an appropriate correction amount (step 30) so as to send the amount to the subtracter 456. In the subtracter 456, the appropriate correction amount $y_k$ is subtracted from the X-ray data $D(LN)_{ij}$ in the linear region after the inverse logarithmic conversion (step 31), the data $D(LN)_{ij}$ being obtained from the pre-correction data memory 451. Data resultant from subtraction is stored in the correction data memory 457. Namely, the X-ray data after the inverse logarithmic conversion read from the pre-correction data memory 451 is subtracted from each scattered ray correction amount identified by i and j, thereby obtaining the total X-ray data $D'(LN)_{ij}$ (i=1, 2, ..., m; j=1, 2, ..., n) from the following expression (2). Each data item $D'(LN)_{ij}$ is stored in the correction data memory 457. Through the above process, the influence of scattered X-rays in the linear region is removed.

$$D'(LN)_{ij} = D(LN)_{ij} - y_k \tag{2}$$

incidentally, in a case where the position of the subject to be measured is altered from the abdomen to the lung, the projection data items P(1,i) (i=1, 2, ...,n) of n channels at the first rotary position are also changed and hence the values $x_k$ of expression 1 is accordingly varied. To cope with this situation, when the measuring position of subject is altered as above, the value $x_k$ is again determined by expression (1) such that $y_k$ is then read from the memory 455 to conduct according thereto the scattered ray correction for the each projection data $D(LN)_{ij}$ by use of expression (2).

X-ray data $D'(LN)_{ij}$ undergone the scattered X-ray correction is data in the linear region and hence cannot be directly adopted in this form to construct an image. The data $D'(LN)_{ij}$ is then subjected to a logarithmic conversion (step 32) to be stored in the main memory 44 or on the magnetic disk 41 of the video diagnoser 4. Thereafter, these data items are transmitted to the image reconstruction processor 46 to reconstruct or to produce a tomogram (step 33). For the reconstructed data, a CT value correction is conducted by the central controller 43 (step 34). According to the obtained data, an image is displayed on the display 47 (step 35). In the video diagnoser 4, the data is transferred via the high-speed internal bus 48. Control of operations and data transfer between the respective constituent components are accomplished by the central controller 43.

In the description above, the scattered ray correction curves are beforehand stored in the correction table memory 455. The curves are essential to remove the influence of scattered X-rays. Next, description will be given of the scattered X-ray correction curves according to the present invention.

The amount of scattered ray correction is obtained according to the following idea.

Figure 7:
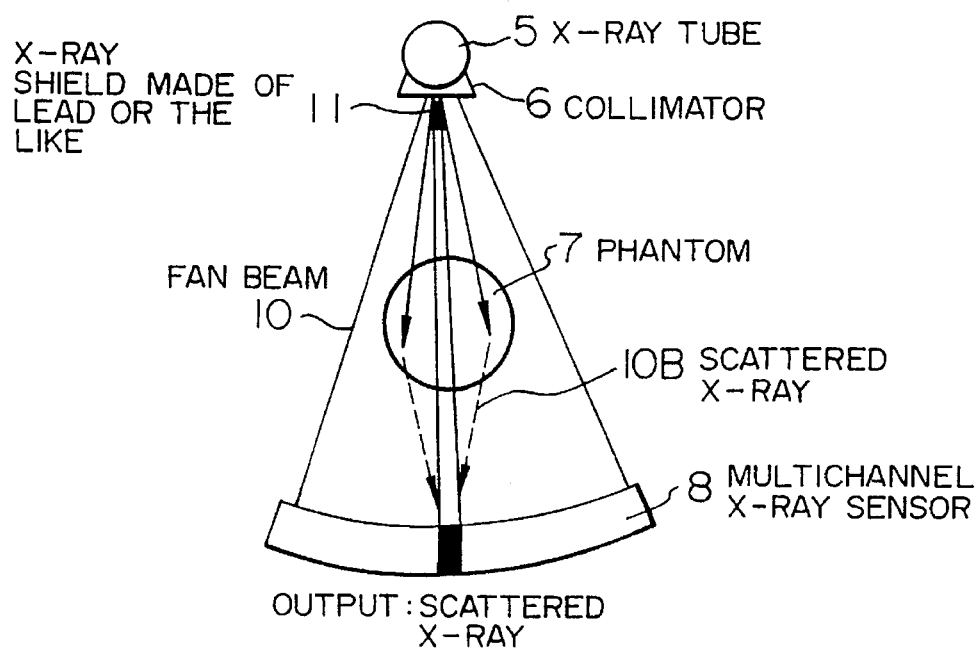
FIG. 7 is a diagram for explaining the principle of attaining the amount of scattered X-rays.

In FIG. 7 corresponding to FIG. 3, an X-ray shield 11 is arranged in a path of the direct X-ray and a water phantom 7 is disposed at the central position in place of the subject. When X-rays are radiated in this state, the direct X-ray does not enter the X-ray sensor channel to which the direct X-ray is incident if the shield 11 is absent. Namely, only scattered X-rays 10B are incident to the pertinent channel, which enables the amount of scattered X-rays to be measured. Repeatedly conducting measurement while altering the size of the phantom 7 and the position of the X-ray shield 11, there is obtained a distribution of intensity of scattered rays. However, this procedure necessitates a large amount of human work and hence it is favorable to adopt a measuring process shown in FIG. 17, which will be described later.

Figure 8:
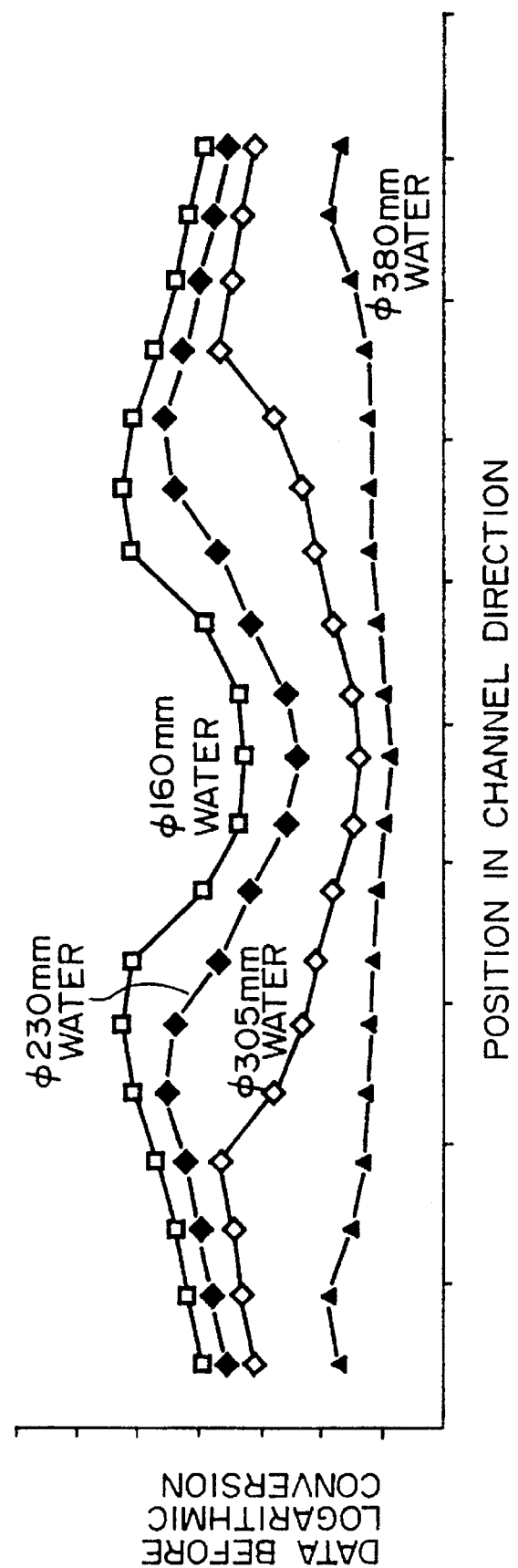
FIG. 8 is a graph showing a relationship between the sensing channel position and the amount of scattered X-rays in various water phantoms.
Figure 17:
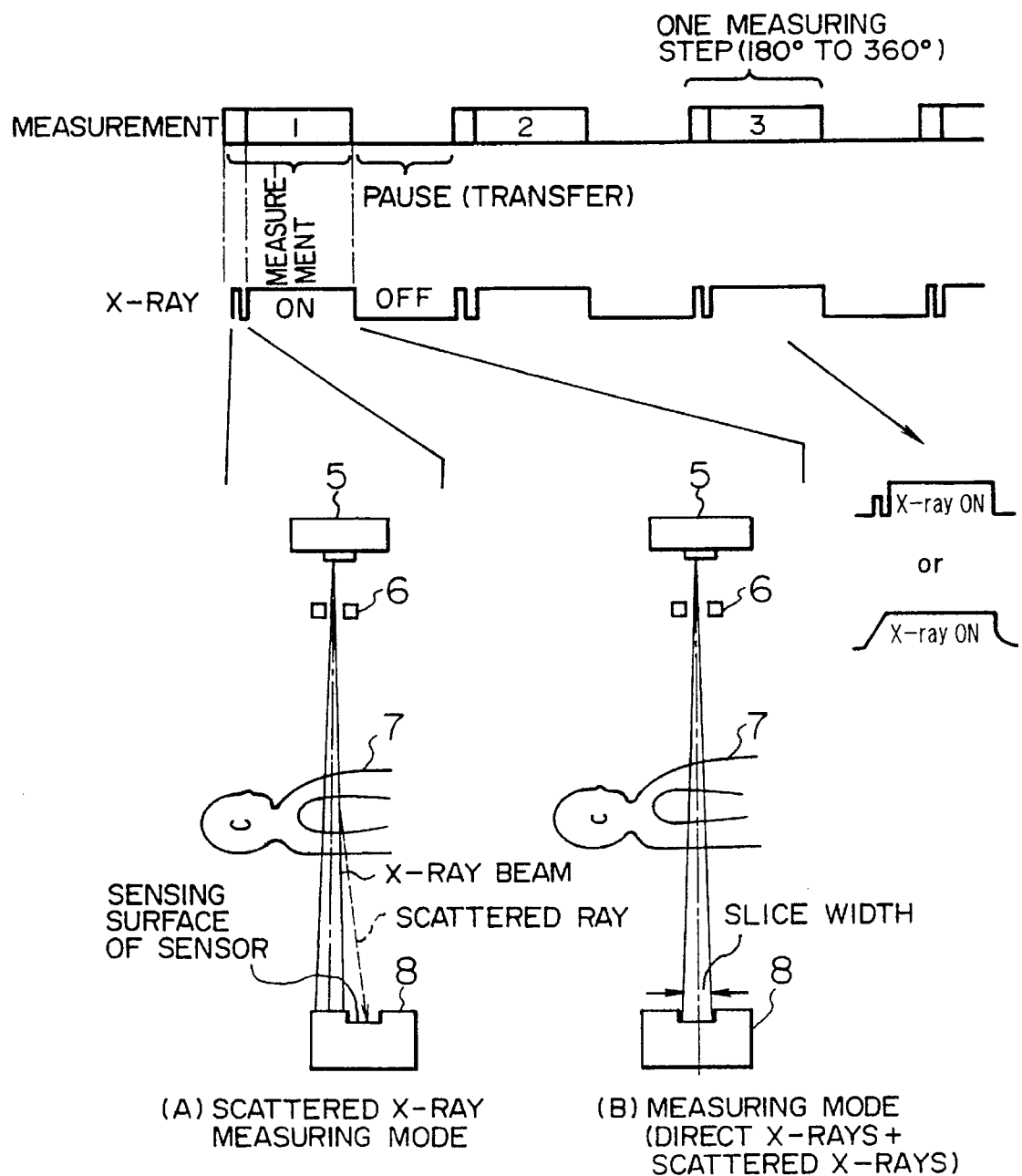
FIG. 17 is a diagram showing an embodiment in which the X-ray receiving position is altered in accordance with the present invention.

FIG. 8 shows an example of intensity distribution of scattered rays attained by the method of FIG. 17. The diameter of the water phantom is set to 160, 230, 305, and 380 millimeters, the abscissa indicates the channel position (number), and the ordinate stands for the scattered X-ray amount (intensity). The intensity is decreased in the central portion and is increased in the peripheral portion of each phantom for the following reasons. Namely, the intensity of scattered X-rays is also attenuated in the phantom. For a phantom of a small diameter or for an identical phantom having a short path for X-rays, the scattered X-ray intensity takes a larger value. Moreover, the greater the phantom diameter is, the weaker the average intensity of the overall X-rays is. To estimate the amount of scattered ray correction, above characteristics are required to be considered. For an appropriate correction of scattered rays, the correction amount is to be determined according to the distribution of scattered ray intensity in the channel direction. However, the effect of correction is rarely deteriorated even when the scattered ray correction is accomplished with a fixed correction amount for all channels for the following reasons. In the present correction method, the scattered ray correction becomes stronger in the central portion of the subject in which the sensor output is decreased in the measuring process, whereas the correction becomes weaker in the periphery of the subject. Moreover, when the subject has a cross section having a shape other than that of a true circle, the contour of scattered ray distribution slightly varies depending on measuring angles. In consideration thereof, the correction amount may be represented as an approximated curve or the correction amount may be weighted so that the correction amount corresponds to the distribution of intensity of scattered rays in the channel direction. In addition, the above correction is effected with a fixed correction amount for each rotary angle. However, the scattered rays basically depend on the size of subject and do not greatly change in quantity with respect to variation in the rotary angle (viewing angle). Consequently, although the precision of correction is slightly lowered when the fixed correction amount is used, there does not take place any particular disadvantage in the scattered ray correction.

Figure 9:
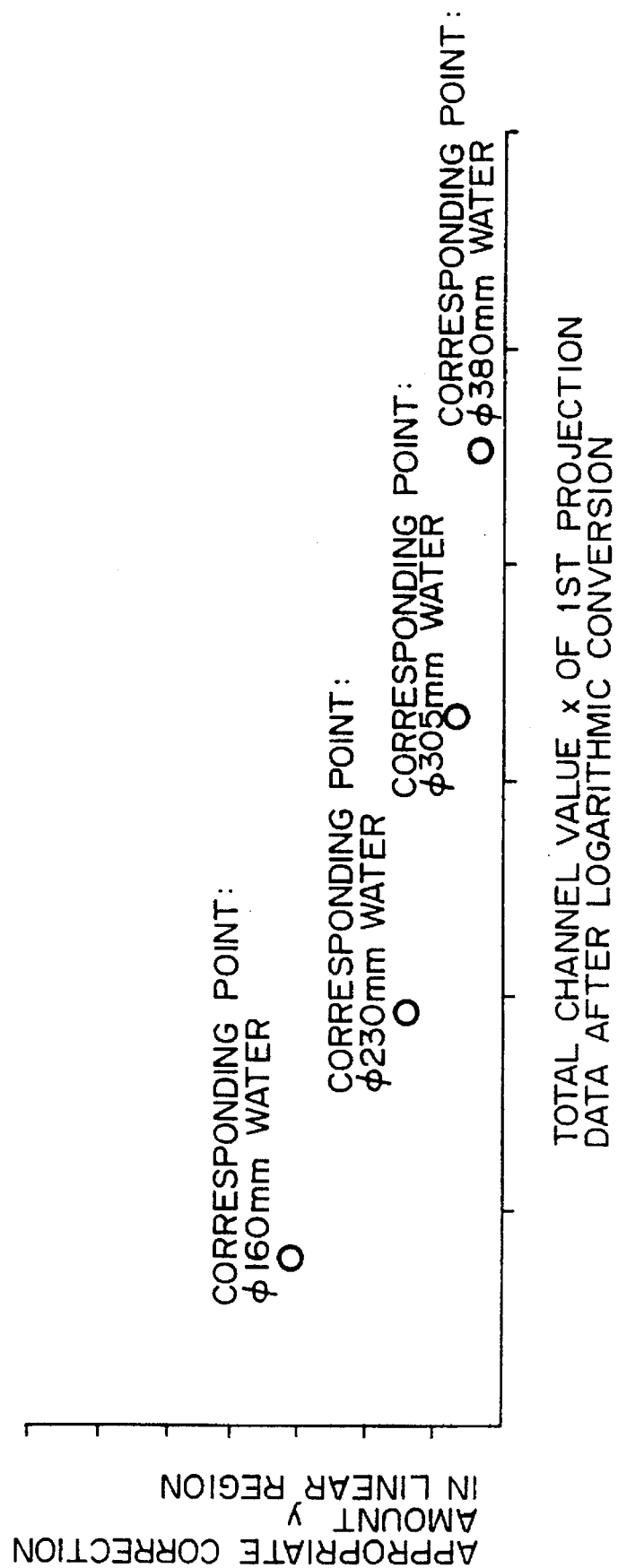
FIG. 9 is a graph showing amounts of scattered ray correction for various water phantoms.

According to the embodiment, to simplify processing and to increase the processing speed, a relationship between the total channel accumulation value x and the scattered ray correction amount y is beforehand attained for a particular rotary angle (for example, the first rotary angle $\theta=0°$) from scattered ray data in the central channel of the water phantom. FIG. 9 shows a distribution of reference sample values for the scattered ray correction determined from the intensity distribution of FIG. 8. The abscissa designates the total channel accumulation value x of the first projection after the logarithmic conversion, whereas the ordinate represents the amount y of scattered ray correction in the linear region. Sampling points (indicated by small circles) respectively corresponds to data items of four phantoms having mutually different diameters.

According to the distribution of reference sample values of FIG. 9, the sampling points are connected to configure a correction curve such that the scattered ray correction is achieved on the basis of the curve.

Subsequently, description will be given of a method of obtaining a function as approximation of the resultant correction curve.

(1) Correction curve: Function of power of total channel accumulation value x

In this example, there is used a function as $$y = a \cdot x^b$$

Constants a and b are decided through approximation by using, for example, the method of least squares according to the sampling points of FIG. 9. The correction curve is similar to a function of measured values and hence the scattered ray correction is appropriately carried out.

(2) Correction curve: Exponential function of total channel accumulation value x In this example, there is used a function as $$y = a \cdot b_x$$

Figure 10:
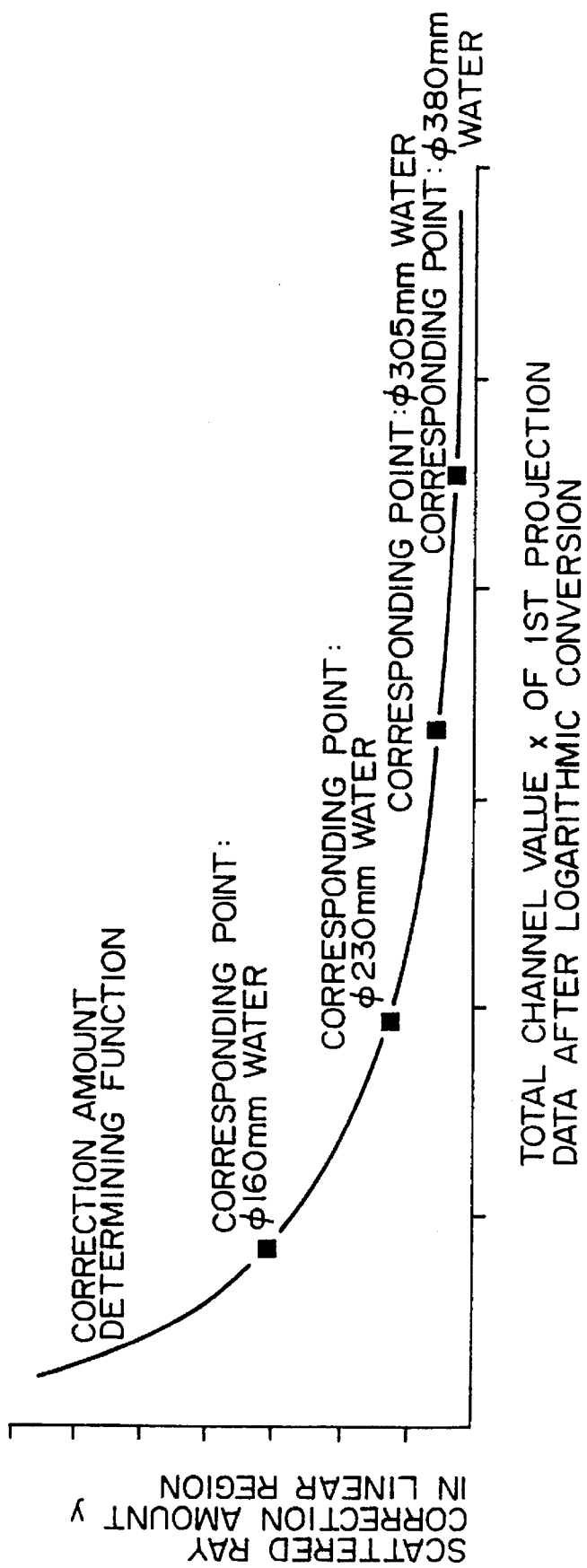
FIG. 10 is a graph of a correction curve in which an exponential function is used as approximation of plotted points of FIG. 9.

Constants a and b are determined through approximation by use of, for example, the method of least squares according to the sampling points of FIG. 9. Selection between the function of power of example (1) and the exponential function of example (2) is achieved depending on the sample data items. FIG. 10 shows an example of the exponential function of example (2).

(3) Correction curve: Function of broken-line

Figure 11:
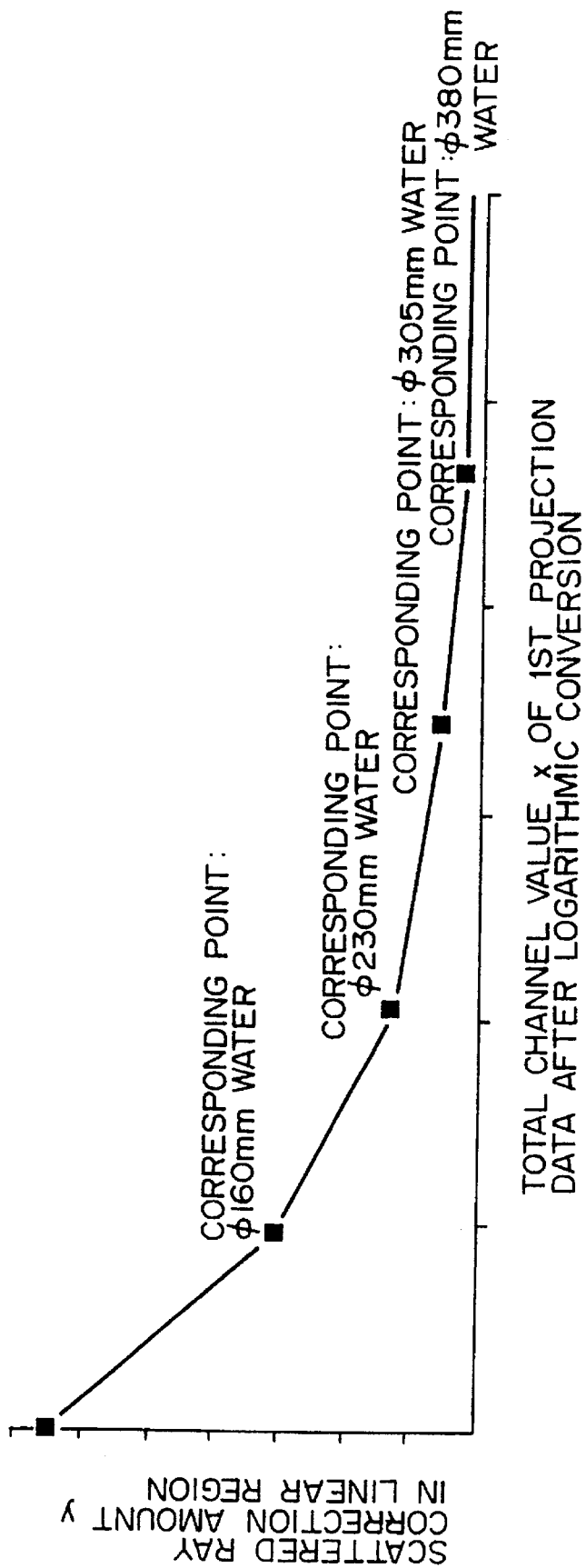
FIG. 11 is a graph of a correction curve in which a linear interpolation is employed as approximation to plotted points of FIG. 9.

FIG. 11 shows a case in which the correction curve is approximately represented by a broken line or a polygonal Line constituted with line segments between the adjacent points of data expressed as (x,y). According to a linear interpolation using the broken-line approximation, there can be attained the required precision of the correction amount. However, for a region of the water phantom corresponding to a diameter smaller than 160 mm, it is necessary to beforehand decide the correction value at a position of x=0 as shown in the diagram.

(4) Correction curve: Step-formed function

Figure 12:
FIG. 12 is a graph of a correction curve in which step-formed discontinuous line segments are adopted as approximation of plotted points of FIG. 9.

Simplifying the polygonal-line approximation of FIG. 11, a step-formed approximation is obtained as shown in FIG. 12. Namely, in a region enclosed by the adjacent points, the value y of either one of the boundaries of the region is used to fixedly determine a correction amount of the region. This resultantly leads to discontinuous lines stepwise arranged.

In this connection, FIGS. 10 to 12 show correction curves determined on the basis of data of FIG. 9. However, the correction curves may be obtained from the quantity of scattered X-rays measured from a phantom made of other than water, namely, polyethylene or acrylic resin having an X-ray absorption coefficient similar to that of the human body.

Moreover, in the description above, there is used the first projection data to calculate the appropriate amount of scattered X-ray correction. However, there may also be used a projection data item at another particular position or a plurality of projection data items to calculate the correction amount in the similar fashion.

As above, the appropriate amount of scattered X-ray correction is decided on the basis of data undergone the phantom calibration of FIG. 4. However, the decision may be conducted according to data before the calibration step.

When an X-ray image is restored through the procedure of FIG. 4 according to measurement of scattered X-rays using phantoms made of water, polyethylene, or acrylic resin and decision of correction curves on the basis of measured results, the problem of mounting the X-ray sensor and that of increase in the production cost can be solved. For a human body as the subject, when measuring X-rays penetrated through the head or abdomen, the influence of scattered X-rays can be removed with a relatively high precision.

While the phantom is an X-ray absorber having a cylindrical shape (a circular cross section), the human body generally has an elliptic cross section. In consequence, the attenuation of incident X-rays in the central portion thereof is smaller in the phantom than in the human body. Furthermore, the human body includes bones and the lung (air) and hence the correction curves attained from the phantoms may possibly have not a satisfactory precision depending on measured positions of the subject.

Figure 13:
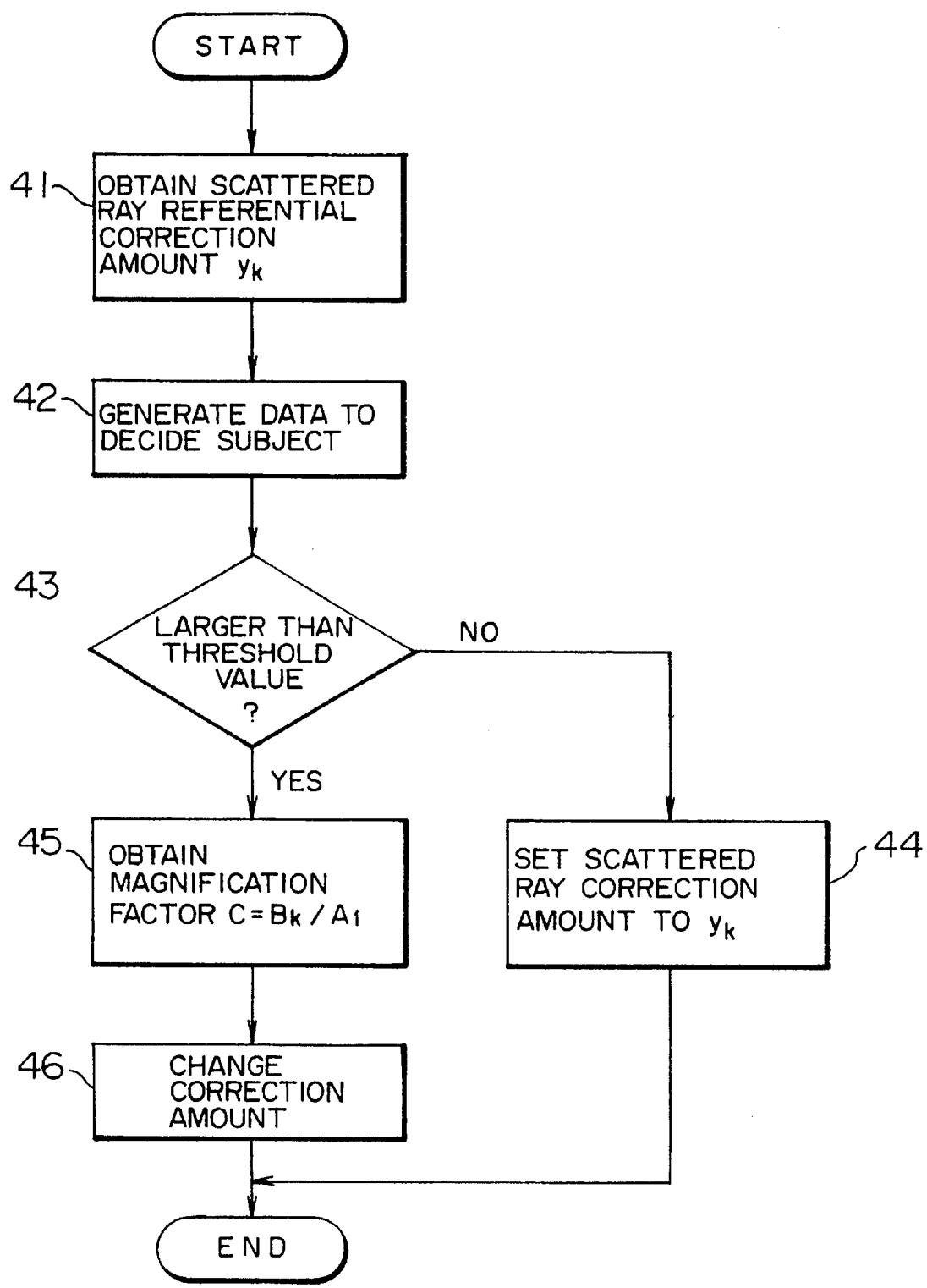
FIG. 13 is a flowchart showing another embodiment of the process of calculating the correction amount of FIG. 4.
Figure 14A:
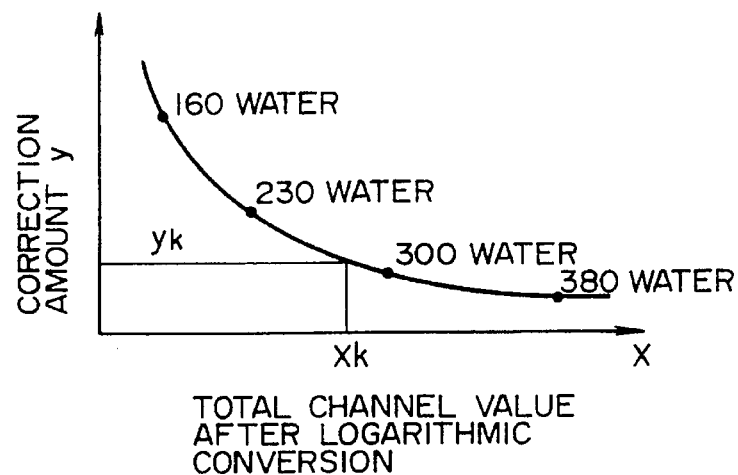
FIGS. 14A and 14B are graphs respectively showing embodiments of the scattered ray correction curves according to the present invention.
Figure 14B:
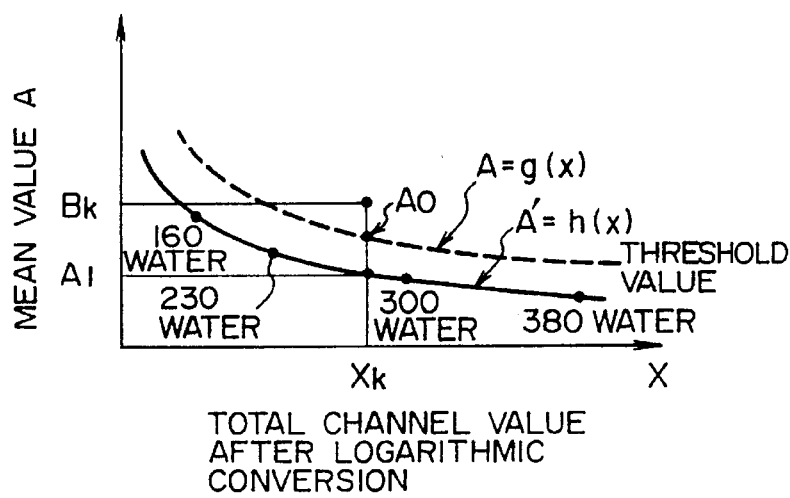
Figure 14C:
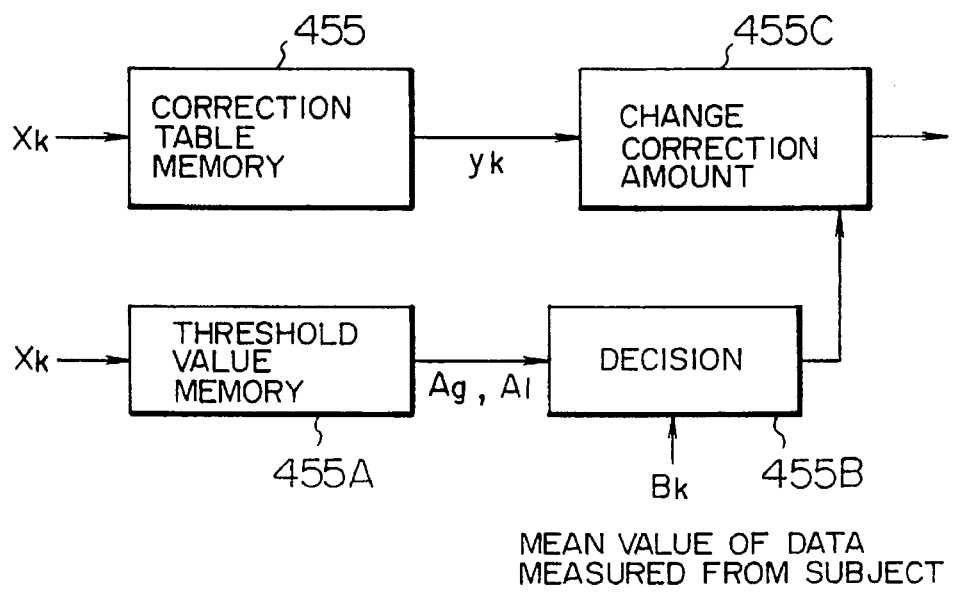
FIG. 14C is a block diagram showing a circuit to obtain the amount of scattered ray correction according to the correction curves of FIGS. 14A and 14B.

To increase the precision of the scattered X-ray correction curves also for the human body, it may also be possible to partly change the correction process above. That is, in step 30 of FIG. 4, the correction amount is calculated from data of absorption of scattered X-rays in the phantom. Since intensity of penetrated X-rays of the human body is higher than that of the phantom, the appropriate correction amount of the human body becomes greater than that of the phantom. To overcome this difficulty, step 30 may be modified as follows. FIG. 13 shows an outline of the modified procedure. FIGS. 14A and 14B are graphs for explaining the operation, whereas FIG. 14C is an embodiment associated therewith. Specifically, FIG. 14C shows a function of correction in the correction table memory 455 of FIG. 2 and FIG. 14B presents a function of a threshold value memory 455A introduced as a new constituent component in FIG. 13.

Description will now be given of the flow of computing the correction amount shown in FIG. 13.

In step 41, according to the correction curves related to the phantom, the amount of scattered ray correction is obtained for the accumulated value $x_k$. This step is equal to step 30 of FIG. 4.

In step 42, there is calculated data to decide that the state of subject is similar to that of the phantom made of water or the like or is quite different therefrom. To this end, there are employed a threshold value function $A=g(x)$ and a phantom mean value function $A'=h(x)$ stored in the threshold memory 455A of FIG. 14B.

In this graph, the abscissa designates the total channel accumulation value x of a first rotary angle (or a particular rotary angle) and the ordinate stands for the threshold values A and the phantom mean value A' obtained on the basis of phantoms having different diameters. The phantom mean value A' is a mean value of X-ray data items obtained, for the first rotary angle of phantoms having different diameters, from the central channel and peripheral channels thereof related to the first rotary angle. Connecting dotted points of the mean values, there is obtained the function $A'=h(x)$. In contrast thereto, the threshold value A is attained by displacing upward the curve of function $A'=h(x)$ by a predetermined distance. The threshold value function $A=g(x)$ is employed for the following reasons.

While the phantom as the reference has a circular cross section, the human body has an elliptic cross section in its central portion, the elliptic contour therein being smaller than the circular shape of the phantom. Consequently, even when the total channel accumulation value x is the same for these two items, the attenuation in the central portion of the human body becomes smaller and hence the value obtained from the central portion is greater than that of the phantom. According to a relationship between the total channel accumulation value x and the attenuation in the central portion resultant from clinical data actually measured, it has been confirmed in most clinical data that the appropriate amount of scattered ray correction for the human body is distributed in the graph which is over the curve of the reference phantom mean value $A'=h(x)$. However, due to bones and the lung (air) in the body, the output values related to the central portion considerably varies in the clinical data. Consequently, to remove the error above, a mean value is calculated from values of a plurality of channels of the central portion to decide that the subject is similar to a human body or a phantom. In place of the mean value, there may be used a total of the values from the plural channels. Furthermore, as the reference for decision, a variance of measured data from the plural channels in the central portion of the sensor may be employed in place of the total value and the mean value. As above, the phantom is made of a uniform substance and has a circular cross section, the output from the channels in the central portion of the X-ray sensor becomes smaller due to the large attenuation. In contrast thereto, the human body is not uniform, namely, made of various substances and has an elliptic cross section, a higher output value is obtained from the central portion. This phenomenon is particularly clear in the lung. Utilizing this characteristic, only the mean value of outputs from the plural channels in the central portion of the X-ray sensor is calculated to determine that the contour of subject is similar to that of a human body or phantom. When the subject is a human body, the output value above is higher than the mean value A' of the phantom. Consequently, in consideration of errors, the threshold value curve $A=g(x)$ of the decision reference is drawn as a dotted-line curve over the mean value curve $A'=h(x)$ through parallel displacement. This curve is decided on the basis of data measured from a human body in advance. In a case where the variance is adopted as the reference, since variation is small in data measured from a phantom, the variance is also minimized and hence the reference curve cannot be obtained. Consequently, to measure data at sampling points, there is employed a human body because the variation and hence the variance is large in the values measured therefrom.

In step 42, using data actually measured from the subject, there is calculated a mean value $B_k$ of the plural channels in the central portion in association with the total channel accumulation value $x_k$ undergone the logarithmic conversion. Moreover, according to the functions of FIG. 14B, there are attained a threshold value $A_0$ and a phantom average value $A_1$ for the value $x_k$.

In step 43, a check is made to decide whether or not the mean value $B_k$ obtained through measurement of the subject is larger than the threshold value $A_0$. If "NO" results, the subject is assumed to have a composition similar to that of the phantom and hence the amount $y_k$ of scattered X-ray correction beforehand attained in step 41 is set as the appropriate amount of scattered ray correction in step 44. However, if "YES" results, the constitution of the subject is assumed to be considerably different from that of the phantom and there is calculated the ratio $C=B_k/A_1$ of the mean value $B_k$ to the phantom mean value $A_1$ in step 45.

In step 46, the appropriate correction amount is changed. Using the ratio or magnification factor C and the correction amount $y_k$ of scattered rays, an appropriate correction amount $y_k'$ is finally obtained for the subject as follows.

$$y_k' = K \cdot C \cdot y_k$$

In this expression, K indicates a gain constant for adjusting the actual effect of correction. The value of K can be beforehand determined from actual data items measured from a human body and a phantom. In this case, the scattered ray correction amount is $y_k'$ in step 30 of FIG. 4.

FIG. 14C shows the processor section to conduct processing of FIG. 13. According to the total channel value $x_k$, the scattered ray correction amount $y_k$ is read from a correction table memory 455 and the mean value $A_0$ is obtained from a threshold value memory 455A. In a decision section 455B, the mean value $A_0$ is compared with the mean value $B_k$ of actual data measured from the subject. If $B_k > A_0$, the correction amount is changed by processing means 455C into output $Y_k'$; otherwise, $y_k$ is outputted therefrom.

In the description of step 42, the ordinate of the graph represents the mean value of outputs from the plural channels in the central portion of the X-ray sensor. However, in place of the mean value, there may be employed a total or a variance of output values from the plural channels.

Moreover, in the case of "YES" in step 43, there is calculated the ratio C to decide the new correction amount $y_k'$. However, when the subject is a portion of a human body, there may be beforehand prepared a different correction curve so as to use values thereof in the case of "YES".

Figure 15:
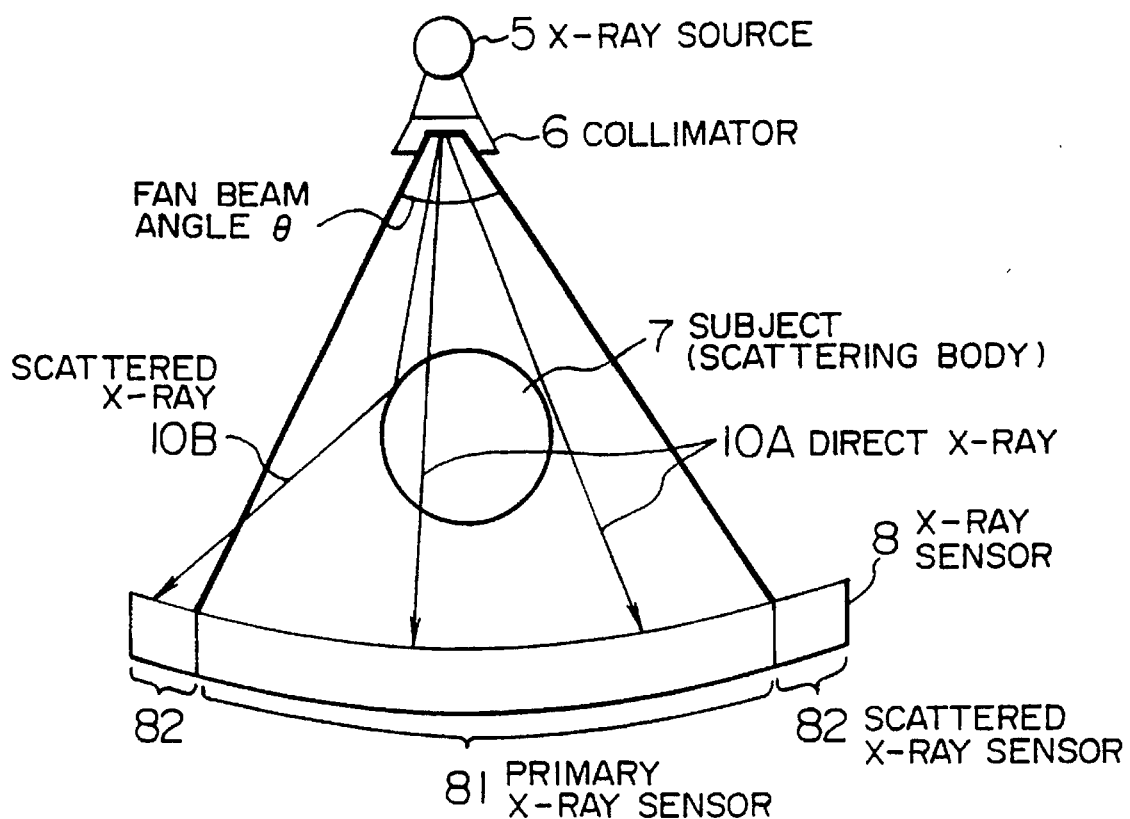
FIG. 15 is a diagram showing an embodiment of an X-ray sensor to obtain the amount of scattered X-rays according to the present invention.

FIG. 15 shows another embodiment of sensing the quantity of scattered X-rays. In this diagram, the range of coverage of the X-ray sensor 8 in the channel direction is relatively larger than that related to the fan beam angle θ of the fun beam 10. Specifically, a group of X-ray sensor elements 81 is covered by the fan beam angle θ, whereas X-ray sensor elements 82 are at positions beyond the fan beam angle θ. An X-ray beam radiated from an X-ray tube 5 is gathered by a collimator 6 into a fan beam having a fan beam angle θ. Namely, direct X-rays are kept retained in the range of the fan angle θ. X-rays of the fan beam 10 enter a subject or a phantom (scattering body) in a measuring space to penetrate therethrough while being gradually attenuated. The direct X-rays 10A containing useful X-ray information reach as signal X-rays the X-ray sensor 8 having sensor elements arranged in a circular arc behind the subject or phantom, the arc having a center thereof at a focal point of the X-ray tube 5. X-ray sensor elements disposed in the coverage area of the fan beam angle θ to receive the direct X-rays function as a primary X-ray sensor 81. On the other hand, X-ray sensor elements disposed beyond the coverage area of the fan beam angle θ to receive only X-rays scattered by the subject serve as X-ray sensors 82.

Each of the X-ray sensors 82 produces an output indicating a quantity of scattered X-rays at the pertinent end position of the X-ray sensor 8. Measuring the outputs from the X-ray sensors 82 for water phantoms having different diameters, there can be obtained scattered ray levels of the channels of the respective end positions. These levels respectively correspond to data items at the end positions in the graph of FIG. 8. Consequently, measuring values of quantities of X-ray scattered from the subject and sensed via the channels at the end positions as shown in FIG. 15, it is possible to estimate the quantity of scattered X-rays of the other channels. Namely, it is unnecessary to arrange a particular sensor to sense scattered X-rays at the central channel of the X-ray sensor 8.

Figure 16A:
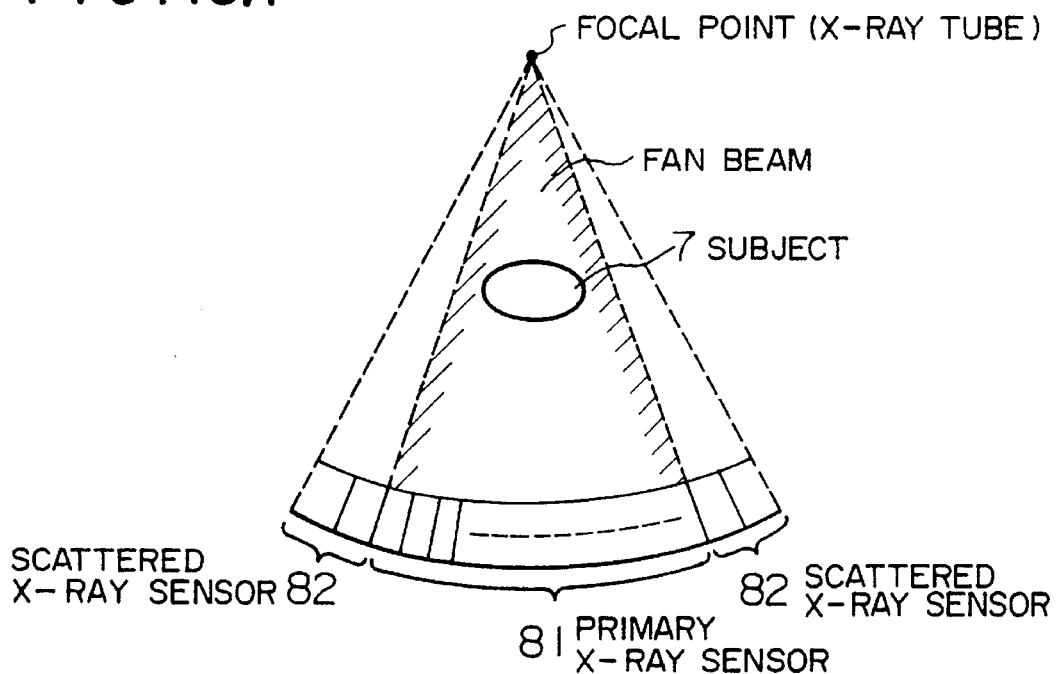
FIGS. 16A and 16B are diagrams respectively showing alternative embodiments of an X-ray sensor to obtain the amount of scattered X-rays according to the present invention.
Figure 16B:
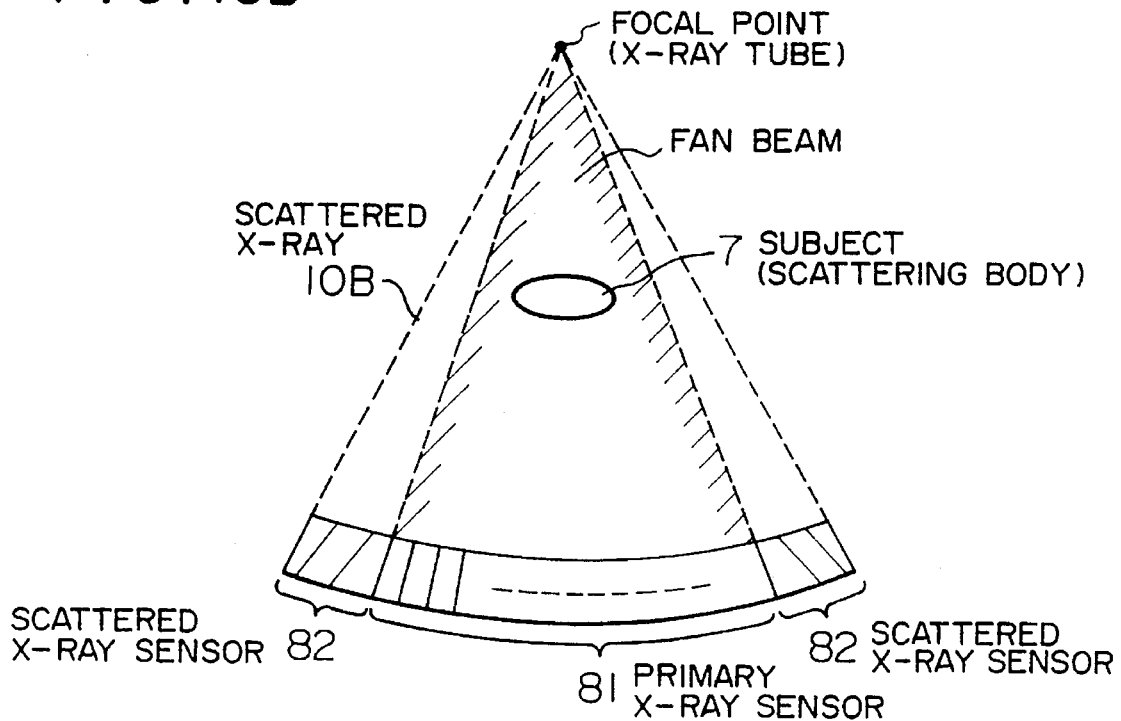

The scattered X-rays can be more effectively obtained via the channels at the end positions by appropriately controlling width (distance between electrode plates) of each sensor elements of the channels. FIGS. 16A and 16B show an example of the configuration. In FIG. 16A, the scattered X-ray sensor 82 of the channel at the end position has a width larger than that of the primary X-ray sensor 81. Since the quantity of scattered X-rays varies only slightly between the channel at the end position and a channel in the vicinity thereof as shown in FIG. 8, the sensitivity of the sensor element can be improved without any considerable deterioration of precision by increasing the width of the sensor element.

FIG. 16B shows an example in which each sensor element of the sensors 82 at the end positions has a center line inclined to direct toward an inside position relative to that of each sensor element of the sensor 81. In this example, the center line of each sensor element of the sensors 82 is oriented toward the center of the scanner opening into which the subject 7 is to be inserted. With the configuration, it is possible to increase the amount of scattered X-rays which can enter the channels at the end positions since the X-rays are not interrupted due to limitation of the width, thereby increasing the sensitivity of the sensor 8.

In the description of the embodiment, the quantity of scattered X-rays is measured by X-ray sensors outside the range of the X-ray fan beam angle θ as shown in FIGS. 15, 16A, and 16B. According to the present invention, however, the scattered X-rays can be measured only by the primary X-ray sensor 81.

FIG. 17 is a diagram for explaining the operation to sense scattered X-rays according to a double sense mode. In this X-ray computerized tomograph, the width of an X-ray beam emitted from an X-ray tube 5 is decreased by a collimator 6 in a direction vertical to the direction in which the channels are arranged, the width being smaller than the longitudinal width of a slit-shaped X-ray sensing surface of an X-ray sensor 8. In a scattered X-ray measuring mode (A) of FIG. 17, the direct X-ray is incident to a position outside the X-ray sensing surface of the sensor 8. Namely, only scattered X-rays are measured via the sensing surface. On the other hand, in a measuring mode (B) of this diagram, direct and scattered X-rays are sensed through the X-ray sensing surface of the sensor 8. The sensor 8 can achieve a high-speed change-over operation between these modes.

To gather X-ray data, a set of these modes is executed in a measuring step (called "scan") such that the scan and a pause (a period of time in which a subject 7 is transferred to the next measuring position) are repeatedly achieved to measure X-rays.

As can be seen from FIG. 17, the measuring operation is first carried out in the scattered X-ray measuring mode for a short period of time. In this period of time, an X-ray scan of all channels of the sensor 8 is accomplished once to several times to collect sensed data items of scattered X-rays. The level of the quantity of X-rays irradiated in this operation is desirably equal to that of the measuring mode. However, when the quantity of illuminated X-rays is reduced to minimize X-rays radiated onto the human body, the quantity of scattered X-rays is required to be corrected in accordance with the reduction in the quantity of illuminated X-rays.

After the X-ray measurement is finished, the system enters the ordinary measuring mode in which X-rays emitted from the X-ray tube 5 onto the subject 7 may be temporarily interrupted or may be kept emitted. (In the case of FIG. 17, the X-rays are temporarily interrupted).

In a video processing step, it is only necessary to subtract the measured amount of scattered X-rays directly from the data obtained in the measuring mode. In this case, since there is not used any phantom, a computerized tomogram can be produced with a higher precision.

As shown in portions (A) and (B) of FIG. 17, the high-speed mode change can be achieved in various methods. FIGS. 18A to 18C shows procedures respectively related thereto. In FIGS. 18A to 18C, the X-ray sensor 8, the collimator 6, and the X-ray tube 5 are respectively transferred in the slicing direction. These operations need only be achieved as follows. The retaining members of the sensor 8, the collimator 6, or the X-ray tube 5 are fixed attached onto a precision control table which is shifted in a single direction by a sliding bearing and a ball screw mechanism, thereby controlling the position thereof.

However, the transfer of the sensor 8, the collimator 6, or the X-ray tube 5 is related to force of inertia, which limits the transfer speed. In the high-speed transfer, it is favorable to use the method of moving the focal point of the X-ray tube 5.

Figure 19A:
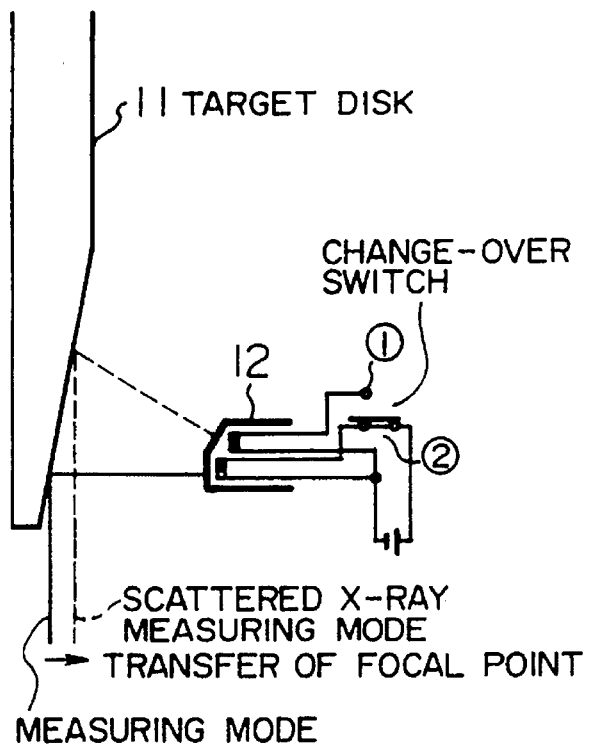
FIGS. 19A to 19C are diagrams respectively showing embodiments in which the X-ray receiving position is altered to attain the amount of scattered X-rays in accordance with the present invention.
Figure 19B:
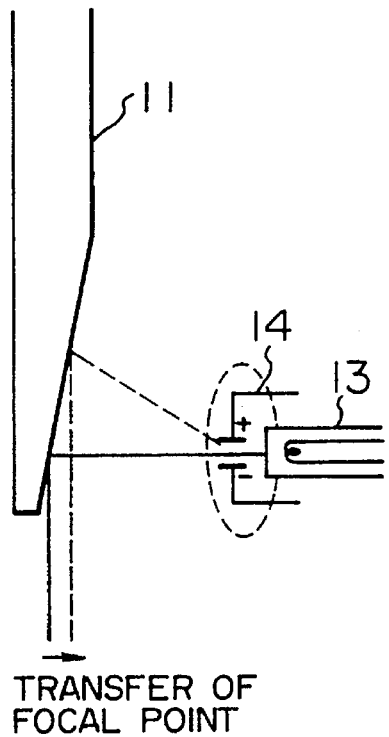
Figure 19C:
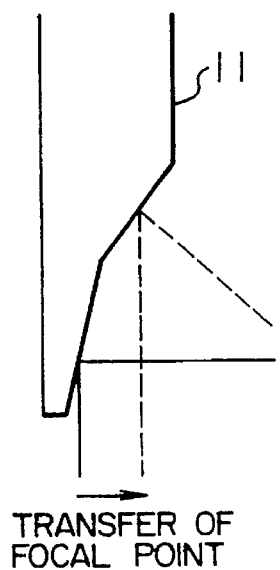

FIGS. 19A to 19C show an example of the method of transferring the focal point of the X-ray tube 5. In FIG. 19A, when a change-over switch is activated to set the switch, which change an electron beam emission source of an electron gun 12 for multiple focal points, to position ①, a filament for scattered X-rays is heated to emit an electron beam onto an upper portion of an inclined surface of a target disk 11. Resultantly, X-rays are irradiated in the downward direction as shown in the drawing. On the other hand, when the switch is set to position ②, the measuring filament is heated to emit the electron beam onto a lower portion of the inclined surface of the target disk 11. As a result, X-rays are irradiated from a position, which is different from that of the scattered X-ray measuring mode, in the downward direction as shown in the diagram.

In the example of FIG. 19B, an electron beam deflector 14 is arranged between an electron gun 13 for a single focal point and a target disk 11. An electric field having the direction shown in FIG. 19B is applied to the deflector 14 such that the electron beam illuminated from the gun 13 is deflected in the direction designated by a dotted line in the diagram. Resultantly, X-rays are irradiated in the direction in which X-rays are emitted in the scattered X-ray measuring mode. When the deflecting voltage is absent, X-rays are irradiated in the X-ray radiating direction of the measuring mode. In FIG. 19C, to increase the discrepancy between focal points, the magnitude of inclination of the target disk 11 is changed.

As a variation of FIG. 19B, there may be adopted a method in which after the electron beam is emitted from the gun 13. The beam direction is altered by applying a voltage to the deflector to illuminate the deflected electron beam onto the inclined flat surface of the target disk. In principle, the method shown in FIG. 19B is suitable for a high-speed operation. According to this method, the scattered X-ray measuring mode can be established by using the rising time of continuous X-rays. Increase in the measuring time due to addition of this mode is hence ignorable.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

We claim:

1. A scattered X-ray correction method for an X-ray computerized tomograph, comprising the steps of:

obtaining from data attained by conducting a logarithmic conversion for measured values of X-rays passed through a first subject a scattered X-ray correction curve indicating a relationship between measured data having undergone the logarithmic conversion and an amount of scattered X-ray correction;

achieving a logarithmic conversion for measured values of X-rays passed through a second subject;

obtaining from measured data of the second subject having undergone the logarithmic conversion and said scattered X-ray correction curve an amount of scattered X-ray correction in a linear region before the logarithmic conversion;

conducting an inverse logarithmic conversion for said measured data of the second subject having undergone the logarithmic conversion and obtaining values in the linear region;

subtracting by a subtracter said amount of scattered X-ray correction from said values in the linear region attained through the inverse logarithmic conversion; and accomplishing a logarithmic conversion for an output from said subtracter and constructing a computerized tomogram related to said second subject.

2. A scattered X-ray correction method according to claim 1, wherein the step of obtaining said scattered X-ray correction curve includes the step of employing a power function, an exponential function, a broken-line function, or a step-formed function as approximation to said relationship between said data having undergone the logarithmic conversion and said correction amount.

3. A scattered X-ray correction method according to claim 1, wherein the step of obtaining said scattered X-ray correction curve includes the step of obtaining an all channel accumulation value of an X-ray sensor as said data having undergone the logarithmic conversion.

4. A scattered X-ray correction method according to claim 1, wherein the step of obtaining said amount of scattered X-ray correction includes the steps of:

obtaining parameters representing a contour of the second subject from said measured data thereof having undergone the logarithmic conversion; and obtaining an appropriate amount of scattered X-ray correction from said parameters and said scattered X-ray correction curve.

5. A scattered X-ray correction method according to claim 4, wherein the step of obtaining said parameters includes the step of obtaining an accumulated value, a mean value, or a variance of outputs from a plurality of channels at a central portion of an X-ray sensor.

6. A scattered X-ray correction method according to claim 1, wherein the step of obtaining said amount of scattered X-ray correction includes the steps of:

obtaining a value $B_k$ representing a contour of the second subject from outputs from a plurality of channels at a central portion of an X-ray sensor;

comparing said value $B_k$ with a predetermined threshold value;

modifying when said value $B_k$ is more than said predetermined threshold value said correction amount obtaining from said scattered X-ray correction curve and outputting a modified correction amount therefrom; and outputting therefrom when said value $B_k$ is equal to or less than said predetermined threshold value said correction amount obtained from said scattered X-ray correction curve as an appropriate scattered X-ray correction amount.

7. A scattered X-ray correction method according to claim 6, wherein the step of obtaining said scattered X-ray correction amount includes the step of obtaining said value $B_k$ from the accumulated value, the mean value, or the variance of outputs from the plural channels at the central portion of said X-ray sensor.

8. An X-ray computerized tomograph comprising:

X-ray sensing means including an X-ray source and a multichannel X-ray sensor for turning around a subject and measuring a quantity of X-rays passed through the subject;

memory means for storing therein a scattered X-ray correction function y=f(x) representing a relationship between an all channel accumulation value after a logarithmic conversion of data obtained by measuring a first subject by said X-ray sensing means and a scattered X-ray correction amount y in a linear region before the logarithmic conversion for the value x;

first logarithmic conversion means for conducting a logarithmic conversion for measured data obtained by measuring a second subject by said X-ray sensing means;

means for obtaining from measured data outputted from said first logarithmic conversion means an accumulation value $x_k$ after a logarithmic conversion of X-ray penetration data via all channels of said X-ray sensing means at a first rotary angle;

means for reading from said memory means a scattered X-ray correction amount $y_k=f(x_k)$ in a linear region corresponding to said accumulation value $x_k$;

subtracting mean for subtracting said scattered X-ray correction amount $y_k$ from data in the linear region obtained by achieving an inverse logarithmic conversion for the measured data after the logarithmic conversion obtained from said second subject;

a second logarithmic conversion means for conducting a logarithmic conversion for data outputted from said subtracting means; and means for reconstructing a computerized tomogram from data outputted from said second logarithmic conversion means.

9. An X-ray computerized tomograph according to claim 8, wherein said memory means includes means for storing therein the scattered X-ray correction curve in the form of a power function, an exponential function, a broken-line function, or a step-formed function.

10. An X-ray computerized tomograph according to claim 8, wherein said multichannel X-ray sensor includes:

a first X-ray sensor arranged in association with a fan beam angle of a fan beam from said X-ray source; and a second X-ray sensor arranged in association with a position beyond the fan beam angle of said X-ray source.

11. An X-ray computerized tomograph according to claim 10, wherein said second X-ray sensor has an X-ray sensing width larger than an X-ray sensing width for each channel of said first X-ray sensor in a direction in which the channels are arranged in said first X-ray sensor.

12. An X-ray computerized tomograph according to claim 10, wherein said second X-ray sensor includes X-ray sensing elements, each said element having a center line oriented to direct toward an inside relative to a direction of a center line of each X-ray sensing element of said first X-ray sensor.

13. An X-ray computerized tomograph according to claim 10, wherein said X-ray sensing means includes:

collimator means for collimating said X-ray beam emitted from said X-ray source to have a width less than a width of an X-ray sensing surface in a direction vertical to a direction in which the channels are arranged in said multichannel X-ray sensor; and means for changing over in a measuring mode said X-ray beam to a position in said X-ray sensing surface and changing over in a scattered X-ray measuring mode said X-ray beam to a position beyond said X-ray sensing surface.

14. An X-ray computerized tomograph according to claim 13, wherein said X-ray beam change-over means includes means for shifting in said scattered X-ray measuring mode said multichannel X-ray sensor in a direction vertical to the channel arranging direction thereof, thereby moving a light receiving position for receiving said X-ray beam to a position beyond said X-ray sensing surface.

15. An X-ray computerized tomograph according to claim 13, wherein said X-ray beam change-over means includes means for shifting in said scattered X-ray measuring mode said X-ray source in a direction vertical to the channel arranging direction thereof, thereby moving a light receiving position for receiving said X-ray beam to a position beyond said X-ray sensing surface.

16. An X-ray computerized tomograph according to claim 13, wherein said X-ray beam change-over means includes means for changing in said scattered X-ray measuring mode a focal position of said X-ray source, thereby moving a light receiving position for receiving said X-ray beam to a position beyond said X-ray sensing surface.

17. An X-ray computerized tomograph comprising:

X-ray sensing means including an X-ray source and a multichannel X-ray sensor for turning around a subject and measuring a quantity of X-rays passed through the subject;

first memory means for storing therein a scattered X-ray correction function y=f(x) representing a relationship between an all channel accumulation value after a logarithmic conversion of data obtained by measuring a first subject by said X-ray sensing means and a scattered X-ray correction amount y in a linear region before the logarithmic conversion for the value x;

second memory means for storing therein a function $A'=h(x)$ representing a relationship between said all channel accumulation value x and a value $A'$ representing a contour of the subject obtained from outputs from a plurality of channels including a central channel of said X-ray sensor;

third memory means for storing therein a threshold function $A=g(x)$ larger in terms of values thereof than said function $A'$;

first logarithmic conversion means for conducting a logarithmic conversion for measured data attained by measuring a second subject by said X-ray sensing means;

means for obtaining from data outputted from said first logarithmic conversion means an accumulation value $x_k$ after a logarithmic conversion of X-ray penetration data via all channels of said X-ray sensing means at a first rotary angle of a sensing system;

means for obtaining from data outputted from said first logarithmic conversion means a value $B_k$ representing a contour of the subject according to outputs from a plurality of channels including the central channel of said X-ray sensor at a second rotary angle of said sensing system;

means for reading from said first, second, and third memory means a scattered X-ray correction amount $y_k=f(x_k)$ corresponding to said all channel accumulation value $x_k$, the value $A'$ representing the contour of the subject, and a threshold value $A_k=g(x_k)$, respectively;

means for comparing said value $B_k$ with said threshold value $A_k$;

means for further correcting when said $B_k$ is more than said threshold value $A_k$ said scattered X-ray correction amount $y_k$ and outputting therefrom a corrected amount $y_k'$ of scattered X-ray correction;

means for outputting therefrom said scattered X-ray correction amount $y_k$ when said $B_k$ is equal to or less than said threshold value $A_k$;

inverse logarithmic conversion means for conducting an inverse logarithmic conversion for measured data after the logarithmic conversion obtained from said second subject, thereby obtaining values in a linear region;

subtracting means for subtracting said corrected amount $y_k'$ of scattered X-ray correction or said scattered X-ray correction amount $y_k$ from data outputted from said inverse logarithmic conversion means;

second logarithmic conversion means for conducting a logarithmic conversion for data outputted from said subtracting means; and means for reconstructing a computerized tomogram from data outputted from said second logarithmic conversion means.

18. An X-ray computerized tomograph according to claim 17, wherein said means for obtaining said contour of the subject includes means for obtaining a mean value, an accumulated value, or a variance of outputs from said plural channels.

19. An X-ray computerized tomograph according to claim 17, wherein said first memory means includes means for storing therein the scattered X-ray correction curve in the form of a power function, an exponential function, a broken-line function, or a step-formed function.

20. An X-ray computerized tomograph according to claim 17, wherein said multichannel X-ray sensor includes:
a first X-ray sensor arranged in association with a fan beam angle of a fan beam from said X-ray source; and
a second X-ray sensor arranged in association with a position beyond the fan beam angle of said X-ray source.

21. An X-ray computerized tomograph according to claim 20, wherein said second X-ray sensor has an X-ray sensing width larger than an X-ray sensing width for each channel of said first X-ray sensor in a direction in which the channels are arranged in said first X-ray sensor.

22. An X-ray computerized tomograph according to claim 20, wherein said second X-ray sensor includes X-ray sensing elements, each said element having a center line oriented to direct toward an inside relative to a direction of a center line of each X-ray sensing element of said first X-ray sensor.

23. An X-ray computerized tomograph according to claim 17, wherein said X-ray sensing means includes:
collimator means for collimating said X-ray beam emitted from said X-ray source to have a width less than a width of an X-ray sensing surface in a direction vertical to a direction in which the channels are arranged in said multichannel X-ray sensor; and
means for changing over in a measuring mode said X-ray beam to a position in said X-ray sensing surface and changing over in a scattered X-ray measuring mode said X-ray beam to a position beyond said X-ray sensing surface.

24. An X-ray computerized tomograph according to claim 23, wherein said X-ray beam change-over means includes means for shifting in said scattered X-ray measuring mode said multichannel X-ray sensor in a direction vertical to the channel arranging direction thereof, thereby moving a light receiving position for receiving said X-ray beam to a position beyond said X-ray sensing surface.

25. An X-ray computerized tomograph according to claim 23, wherein said X-ray beam change-over means includes means for shifting in said scattered X-ray measuring mode said X-ray source in a direction vertical to the channel arranging direction thereof, thereby moving a light receiving position for receiving said X-ray beam to a position beyond said X-ray sensing surface.

26. An X-ray computerized tomograph according to claim 23, wherein said X-ray beam change-over means includes means for changing in said scattered X-ray measuring mode a focal position of said X-ray source, thereby moving a light receiving position for receiving said X-ray beam to a position beyond said X-ray sensing surface.

* * * * *